(12) United States Patent
Charrier et al.

(10) Patent No.: US 8,071,618 B2
(45) Date of Patent: *Dec. 6, 2011

(54) CASPASE INHIBITORS AND USES THEREOF

(75) Inventors: Jean Damien Charrier, Wantage (GB); Michael Mortimore, Burford (GB); John Studley, Witney (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/562,277

(22) Filed: Sep. 18, 2009

(65) Prior Publication Data

US 2010/0137359 A1    Jun. 3, 2010

Related U.S. Application Data

(63) Continuation of application No. 10/743,563, filed on Dec. 22, 2003, now Pat. No. 7,612,091.

(60) Provisional application No. 60/435,133, filed on Dec. 20, 2002.

(51) Int. Cl.
*C07D 217/24* (2006.01)
*A61K 31/472* (2006.01)

(52) U.S. Cl. ........................................ 514/309; 546/141

(58) Field of Classification Search .................. None
See application file for complete search history.

(56) References Cited

U.S. PATENT DOCUMENTS

| 4,728,647 | A | 3/1988 | Benavides et al. |
| 5,656,627 | A | 8/1997 | Bemis et al. |
| 5,716,929 | A | 2/1998 | Bemis et al. |
| 5,756,466 | A | 5/1998 | Bemis et al. |
| 5,847,135 | A | 12/1998 | Bemis et al. |
| 5,973,111 | A | 10/1999 | Bemis et al. |
| 6,025,147 | A | 2/2000 | Bemis et al. |
| 6,103,711 | A | 8/2000 | Bemis et al. |
| 6,420,522 | B1 | 7/2002 | Bemis et al. |
| 6,525,076 | B1 | 2/2003 | Zhu et al. |
| 7,612,091 | B2 * | 11/2009 | Charrier et al. ............. 514/309 |
| 2003/0162993 | A1 | 8/2003 | Mortimore et al. |
| 2004/0019017 | A1 | 1/2004 | Mortimore et al. |
| 2004/0048797 | A1 | 3/2004 | Miller et al. |
| 2004/0242494 | A1 | 12/2004 | Brenchley et al. |

FOREIGN PATENT DOCUMENTS

| DE | 232699 A1 | 2/1986 |
| EP | 0761680 A2 | 12/1997 |
| EP | 1203766 A2 | 5/2002 |
| WO | 95/35308 A1 | 12/1995 |
| WO | 9603982 A1 | 2/1996 |
| WO | 96/40647 A1 | 12/1996 |
| WO | 97/22619 A2 | 6/1997 |
| WO | 98/16502 A1 | 4/1998 |
| WO | 98/16505 A1 | 4/1998 |
| WO | 98/18781 A2 | 5/1998 |
| WO | 00/67746 A1 | 11/2000 |
| WO | 00/68188 A1 | 11/2000 |
| WO | 01/42216 A2 | 6/2001 |
| WO | 01/94351 A1 | 12/2001 |
| WO | 03042169 A2 | 5/2003 |
| WO | 03/068242 A1 | 8/2003 |
| WO | 2004/002961 A1 | 1/2004 |
| WO | 2004/058718 A1 | 7/2004 |
| WO | 2006/005796 A1 | 6/2006 |

OTHER PUBLICATIONS

Dec. 27, 2004 Office Action from U.S. Appl. No. 10/609,147.
Jun. 12, 2003 Office Action from U.S. Appl. No. 10/166,437.
Feb. 26, 2004 Office Action from U.S. Appl. No. 10/166,437.
Jan. 26, 2007 Office Action from U.S. Appl. No. 10/166,437.
Golec, et al., "Structure-Based Design on Non-Peptidic Pyridone Aldehydes as Inhibitors of Interleukin-1β Converting Enzyme", Bioorganic & Medicinal Chemistry Letters (1997), vol. 7, No. 17, pp. 2181-2186.
Semple, et al., "Peptidomimetic Aminomethylene Ketone Inhibitors of Interleukin-1β-Converting Enzyme (ICE)", Bioorganic & Medicinal Chemistry Letters (1998), vol. 8, pp. 959-964.
Semple, G., et al., "Pyridone-Based Peptidomimetic Inhibitors of Interleukin-1β-Converting Enzyme (ICE)," Bioorganic & Medicinal Chem. Letters, vol. 7, No. 10, pp. 1337-1342 (1997). Livingston, D.J., "In Vitro and In Vivo Studies of Ice Inhibitors," J. of Cell. Biochem., 64(1):19-26 (1997).
Husain, M.I. and Singh, E., "Some New 2-Aryloxymethyl-3-alpha-substituted Carboxymethyl-6,8-substituted-4-Quinazolones As Possible Anticonvulsants,", Pharmazie, 37(6):408-410 (1982).
Hussian, M.I. and Amir, M., "Some Newer Quinazolones as Possible Anticonvulsants," J. Chem. Soc. Pak, 6 (4):211-215 (1984).

(Continued)

*Primary Examiner* — Zinna Northington Davis
(74) *Attorney, Agent, or Firm* — Jennifer G. Che

(57) ABSTRACT

The present invention provides a compound of formula I:

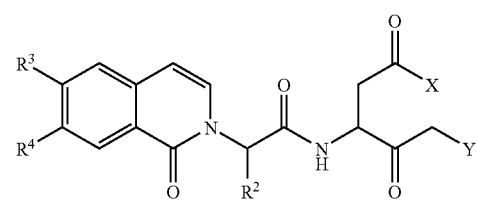

wherein:
X is —OR$^1$ or —N(R$^5$)$_2$,
Y is halo, trifluorophenoxy, or tetrafluorophenoxy;
R$^1$ is:
C$_{1-6}$ straight chained or branched alkyl, alkenyl, or alkynyl, wherein the alkyl, alkenyl, or alkynyl is optionally substituted with optionally substituted aryl, CF$_3$, CI, F, OMe, OEt, OCF$_3$, CN, or NMe$_2$;
C$_{1-6}$ cycloalkyl, wherein 1-2 carbon atoms in the cycloalkyl is optionally replaced with —O— or —NR$^5$—;
R$^2$ is C$_{1-6}$ straight chained or branched alkyl;
Art Unit 1625
R$^3$ is hydrogen, halo, OCF$_3$, CN, or CF$_3$;
R$^4$ is hydrogen, halo, OCF$_3$, CN, or CF$_3$; and
each R$^5$ is independently H, C$_{1-6}$ straight chained or branched alkyl, aryl, —O—C$_{1-6}$ straight chained or branched alkyl, or —O-aryl. The present invention also provides pharmaceutical compositions and methods using such compositions for treating a caspase-mediated disease, particularly in the central nervous system.

2 Claims, No Drawings

OTHER PUBLICATIONS

Canonne, P., et al., "Synthesis of chiral 3-substituted 2,4(1H,3H)-quinazolinediones," Heterocycles, 36(6):1305-1314 (1993).

Gouilleux, L, et al., "Solid Phase Synthesis of Chiral 3-substituted Quinazoline-2, 4-diones," Tetrahedron Letters, 37 (39):7031-7034 (1996).

Gordeev, M.F., et al., "A General and Efficient Solid Phase Synthesis of Quinazoline-2, 4-diones," Tetrahedron Letters, 38(10):1729-1732 (1997).

Prokai-Tatrai, K., et al., "Prodrugs to Enhance Central Nervous System Effects of TRH-like Peptide pGlu-Glu-Pro-NH2," Bioorg. Med. Chem. Lett., 13:1011-1014 (2003).

Narasimhan, R.S., "Synthetic Application of Lithiation Reactions; IX. A Simplified Synthesis of Isocoumarin," Synthesis, 12: 797 (1975).

Kinder, M.A., et al., "Solid State Photochemistry of Isocoumarins and Isothiocoumarins," Tetrahedron 56: 6763-6767 (2000).

Revesz, L., et al., "Synthesis of P1 Aspartate-Based Peptide Acyloxymethyl and Fluoromethyl Ketones as Inhibitors of Interleukin-1β-Converting Enzyme," Tetrahedron Letters, 35 (52):9693-9696 (1994).

Golstein, P., "Cell death in us and others", Science, 281 (5381), 1283 (1998).

Ellis, et al., "Mechanisms and functions of cell death", Annual Review Cell Biology, 7, 663 (1991).

Thornberry, N.A., "Key Mediators of Apoptosis", Chemical Biology, 5, R97-R103 (1998).

Yaoita, H., et al., "Attenuation of ischemia/reperfusion injury in rats by a caspase inhibitor", Circulation, 97, 276-281 (1998).

Endres, M., et al., "Attenuation of delayed neuronal death after mild focal ischemia in mice by inhibition of the caspase family", Journal of Cerebral Blood Flow and Metabolism, 18, 238-247 (1998).

Cheng, Y., et al., "Caspase inhibitor affords neuroprotection with delayed administration in a rat model of neonatal hypoxic-ischemic brain injury", Journal of Clinical Investigation, 101, 1992-1999 (1998).

Yakovlev, A.G., et al., "Activation of CPP32-like caspases contributes to neuronal apoptosis and neurological dysfunction after traumatic brain injury", The Journal of Neuroscience, 17, 7415-7424 (1997).

Rodriguez, I., et al., "Systemic injection of a tripeptide inhibits the intracellular activation of CPP32-like proteases in vivo and fully protects mice against fas-mediated fulminant liver destruction and death", Journal of Experimental Medicine, 184, 2067-2072 (1996).

Grobmyer, S.R., et al., "Peptidomimetic fluoromethylketone rescues mice from lethal endotoxic shock", Molecular Medicine, 5, 585-594 (1999).

Plattner, J.J., et al., "Obstacles to Drug Development from Peptide Leads", Drug Discovery Technologies, ch. 5, pp. 93-126 (1990).

Wilson, K., et al., "Structure and mechanism of interleukin-1β converting enzyme", 370, 270-275 (1994).

Lazebnik, Y.A., et al., "Cleavage of poly(ADP-ribose) polymerase by a proteinase with properties like ICE", Nature, 371, 346-347 (1994).

Greig, N.H., et al., "Physicochemical and pharmacokinetic parameters of seven lipophilic chlorambucil esters designed for brain penetration", Cancer Chemotherapy, 25, 311-319 (1990).

Tejani-Butt, S.M., et al., "Evaluation of mono-and dibenzoyl esters of dopamine as potential pro-drugs for dopamine in the central nervous system", Arch. Pharmacology, 338(5):497-503 (1988).

Prokai-Tatrai, K., et al., "Brain-targeted delivery of a leucine-enkephalin analogue by retrometabolic design", J. Med. Chem., 39, 4775-4782 (1996).

Ishikura, T., et al., "Drug delivery to the brain. DOPA prodrugs based on a ring-closure reaction to quaternary thiazolium compounds", Int. J. Pharmaceutics, 116, 51-63 (1995).

Bonina, F.P., et al., "Synthesis, stability, and pharmacological evaluation of nipecotic acid prodrugs", J. Pharm. Sci., 88(5):561-567 (1999).

Battaglia, G., et al., "Systemically administered d-glucose conjugates of 7-chlorokynurenic acid are centrally available and exert anticonvulsant activity in rodents", Brain Res., 860, 149-156 (2000).

Caba, J.M., et al., "Solid-phase total synthesis of trunkamide A", J. Org. Chem., 66, 7568-7574 (2001).

Schierle, G., et al., "Caspase inhibition reduces apoptosis and increases survival of nigral transplants", Naturs Medicine, 5, 97-100 (1999).

Anderson, B.D., "Prodrugs for Improved CNS Delivery", Advanced Drug Delivery Reviews, 19, 171-202 (1996).

Patent Assignment Abstract of Title for U.S. Appl. No. 10/609,147 which corresponds to WO 2004/002961, filed Jun. 27, 2003.

* cited by examiner

CASPASE INHIBITORS AND USES THEREOF

This application is a continuing application of U.S. patent application Ser. No. 10/743,563, filed on Dec. 22, 2003 now U.S. Pat. No. ;7,612,091, which claims the benefit of U.S. Provisional Application Ser. No. 60/435,133, filed Dec. 20, 2002, which is incorporated herein by reference.

FIELD OF THE INVENTION

This invention relates to compounds, and compositions thereof, that are prodrugs of caspase inhibitors.

This invention also relates to processes for preparing these caspase inhibitor prodrugs.

This invention further relates to pharmaceutical compositions comprising said prodrugs and to the use of the compounds and compositions thereof for the treatment of diseases and disorders related to inflammatory or degenerative conditions.

BACKGROUND OF THE INVENTION

Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, ischemic diseases and certain neurodegenerative disorders [see generally *Science,* 281, pp. 1283-1312 (1998); Ellis et al., *Ann. Rev. Cell. Biol.,* 7, p. 663 (1991)].

Caspases are a family of cysteine protease enzymes that are key mediators in the signaling pathways for apoptosis and cell disassembly [N. A. Thornberry, *Chem. Biol.,* 5, pp. R97-R103 (1998)]. These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

The utility of caspase inhibitors to treat a variety of mammalian disease states associated with an increase in cellular apoptosis has been demonstrated using peptidic caspase inhibitors. For example, in rodent models, caspase inhibitors have been shown to reduce infarct size and inhibit cardiomyocyte apoptosis after myocardial infarction, to reduce lesion volume and neurological deficit resulting from stroke, to reduce post-traumatic apoptosis and neurological deficit in traumatic brain injury, to be effective in treating fulminant liver destruction, and to improve survival after endotoxic shock [H. Yaoita et al., *Circulation,* 97, pp. 276-281 (1998); M. Endres et al., *J. Cerebral Blood Flow and Metabolism,* 18, pp. 238-247, (1998); Y. Cheng et al., *J. Clin. Invest.,* 101, pp. 1992-1999 (1998); A. G. Yakovlev et al., *J. Neurosci.,* 17, pp. 7415-7424 (1997); I. Rodriquez et al., *J. Exp. Med.,* 184, pp. 2067-2072 (1996); Grobmyer et al., *Mol. Med.,* 5, p. 585 (1999)]. However, due to their peptidic nature, such inhibitors are typically characterized by undesirable pharmacological properties, such as poor cellular penetration and cellular activity, poor oral absorption, poor stability and rapid metabolism [J. J. Plattner and D. W. Norbeck, in *Drug Discovery Technologies,* C. R. Clark and W. H. Moos, Eds. (Ellis Horwood, Chichester, England, 1990), pp. 92-126]. This has hampered their development into effective drugs. These and other studies with peptidic caspase inhibitors have demonstrated that an aspartic acid residue is involved in a key interaction with the caspase enzyme [K. P. Wilson et al., *Nature,* 370, pp. 270-275 (1994); Lazebnik et al., *Nature,* 371, p. 346 (1994)].

Accordingly, peptidyl and non-peptidyl aspartic acid compounds are useful as caspase inhibitors. For examples, WO96/03982 reports azaaspartic acid analogs effective as interleukin-1β converting enzyme ("ICE") inhibitors.

However, due to their acidic nature such peptidic and non-peptidyl aspartic acid derivatives are charged at physiological pH. This has inhibited their ability to cross the blood brain barrier and to penetrate cells at therapeutically useful levels.

Accordingly, it would be advantageous to have drug derivatives that are targeted at the diseased organs, especially the brain and central nervous system. In addition, it would be advantageous to have drug derivatives that are targeted at the diseased cells rather than at healthy cells, thus reducing undesirable side-effects.

The use of prodrugs to impart desired characteristics such as increased bioavailability or increased site-specificity for known drugs is a recognized concept. The use of pro-drugs to deliver compounds across the Blood-Brain barrier (BBB) is also well known. brain penetration (Cancer Chemother. Pharmacol. (1990), Bradley D. Anderson, "Prodrugs for Improved CNS Delivery" in Advanced Drug Delivery Reviews (1996), 19, 171-202 provides a review of the area. In particular, the use of alkyl esters of chloambucil have been used to enhance 25, 311-319); the use of benzoyl esters of dopamine have been used to enhance delivery across BBB (Naunyn-Schmiedeberg's Arch. Pharmacol., (1988), 338(5), 497-503); lipophilic esters of a leucine-enkephalin analogue have been used for brain-targeted delivery (J. Med. Chem., (1996), 39(24), 4775-4782). Disulphide-based esters of L-DOPA have been shown to increase brain levels of DOPA in the rat brain up to 30 fold (Int. J. Pharmaceutics, (1995), 116, 51-63). The tyrosine ester of nipecotic acid showed in vivo effects consistent with BBB penetration (J. Pharma. Sci., (1999), 88(5), 561) and D-glucose esters of 7-chlorokynurenic acid are available to CNS and are anti-convulsive in vivo (Brain Res., (2000), 860, 149-156.

A need nevertheless exists for prodrugs of caspase inhibitors that have the ability to cross the blood brain barrier and penetrate the brain and central nervous system at therapeutically useful levels.

SUMMARY OF THE INVENTION

The present invention provides a compound of formula I:

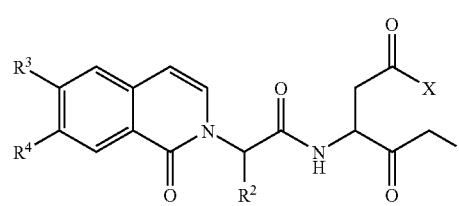

wherein:

X is —OR$^1$ or —N(R$^5$)$_2$,

Y is halo, trifluorophenoxy, or tetrafluorophenoxy;

$R^1$ is:

- $C_{1-6}$ straight chained or branched alkyl, alkenyl, or alkynyl, wherein the alkyl, alkenyl, or alkynyl is optionally substituted with aryl, $CF_3$, Cl, F, OMe, OEt, $OCF_3$, CN, or $NMe_2$;
- $C_{1-6}$ cycloalkyl, wherein 1-2 carbon atoms in the cycloalkyl is optionally replaced with —O— or —$NR^5$—;

$R^2$ is $C_{1-6}$ straight chained or branched alkyl;

$R^3$ is hydrogen, halo, $OCF_3$, CN, or $CF_3$;

$R^4$ is hydrogen, halo, $OCF_3$, CN, or $CF_3$; and each $R^5$ is independently H, $C_{1-6}$ straight chained or branched alkyl, aryl, —O—$C_{1-6}$ straight chained or branched alkyl, or —O-aryl.

The present invention also provides processes for preparing these compounds, compositions, pharmaceutical compositions, and methods using such compounds and compositions for inhibiting caspases and methods for treating caspase-mediated diseases, particularly a caspase-mediated diseases in the central nervous system.

DETAILED DESCRIPTION OF THE INVENTION

The present invention provides pro-drug esters, amides, or hydroxamides of caspase inhibitors that have an improved ability, relative to the corresponding drug, of crossing the blood-brain barrier. Inside the blood-brain barrier, the pro-drugs have the ability to undergo cleavage and provide a caspase inhibitor within the brain.

According to one embodiment (A), this invention provides a compound of formula I:

wherein:

X is —$OR^1$ or —$N(R^5)_2$,

Y is halo, trifluorophenoxy, or tetrafluorophenoxy;

$R^1$ is:

- $C_{1-6}$ straight chained or branched alkyl, alkenyl, or alkynyl, wherein the alkyl, alkenyl, or alkynyl is optionally substituted with aryl, $CF_3$, Cl, F, OMe, OEt, $OCF_3$, CN, or $NMe_2$;
- $C_{1-6}$ cycloalkyl, wherein 1-2 carbon atoms in the cycloalkyl is optionally replaced with —O— or —$NR^5$—;

$R^2$ is $C_{1-6}$ straight chained or branched alkyl;

$R^3$ is hydrogen, halo, $OCF_3$, CN, or $CF_3$;

$R^4$ is hydrogen, halo, $OCF_3$, CN, or $CF_3$; and each $R^5$ is independently H, $C_{1-6}$ straight chained or branched alkyl, aryl, —O—$C_{1-6}$ straight chained or branched alkyl, or —O-aryl.

According to another embodiment (B), this invention provides compound of formula I:

wherein:

X is —$OR^1$ or —$N(R^5)_2$,

Y is halo, trifluorophenoxy, or tetrafluorophenoxy;

$R^1$ is:

- $C_{1-6}$ straight chained or branched alkyl, alkenyl, or alkynyl, wherein the alkyl, alkenyl, or alkynyl is optionally substituted with aryl, $CF_3$, Cl, F, OMe, OEt, $OCF_3$, CN, or $NMe_2$;
- $C_{1-6}$ cycloalkyl, wherein 1-2 carbon atoms in the cycloalkyl is optionally replaced with —O— or —$NR^5$—;

$R^2$ is $C_{1-6}$ straight chained or branched alkyl;

$R^3$ is hydrogen, halo, $OCF_3$, CN, or $CF_3$;

$R^4$ is hydrogen, halo, $OCF_3$, CN, or $CF_3$; and $R^5$ is H, $C_{1-6}$ straight chained or branched alkyl, or —O—$C_{1-6}$ straight chained or branched alkyl; provided that if:

Y is F;

$R^2$ is isopropyl, $R^3$ is hydrogen, and $R^4$ is Cl; or $R^2$ is ethyl, $R^3$ is hydrogen, and $R^4$ is Cl or $CF_3$; or $R^2$ is ethyl, $R^3$ is Cl or $CF_3$, and $R^4$ is hydrogen; then $R^1$ is not t-butyl; and if Y is 2,3,5,6-tetrafluorophenoxy;

$R^2$ is ethyl; and $R^3$ and $R^4$ are each hydrogen; or $R^3$ is hydrogen and $R^4$ is Cl or $CF_3$; or $R^3$ and $R^4$ are each Cl; then $R^1$ is not t-butyl.

The present invention also provides in another embodiment (C) a compound of formula I:

wherein:

Y is halo, trifluorophenoxy, or tetrafluorophenoxy;

$R^1$ is $C_{1-6}$ straight chained or branched alkyl optionally substituted with phenyl or $CF_3$;

$R^2$ is $C_{1-6}$ straight chained or branched alkyl;

$R^3$ is hydrogen, halo, $OCF_3$, CN, or $CF_3$; and $R^4$ is hydrogen, halo, $OCF_3$, CN, or $CF_3$.

An alternative form of embodiment C provides that if:

Y is F;

$R^2$ is ethyl; and $R^3$ is hydrogen and $R^4$ is Cl or $CF_3$; or $R^3$ is Cl or $CF_3$ and $R^4$ is hydrogen; then $R^1$ is not t-butyl; and if
Y is 2,3,5,6-tetrafluorophenoxy;
$R^2$ is ethyl; and
$R^3$ and $R^4$ are each hydrogen; or
$R^3$ is hydrogen and $R^4$ is Cl; or
$R^3$ and $R^4$ are each Cl; then
$R^1$ is not t-butyl.

According to another embodiment, the present invention provides a compound of formula IA':

IA' wherein X, $R^2$, $R^3$, and $R^4$ are as defined in any of the embodiments herein.

According to another embodiment, the present invention provides a compound of formula IA:

IA wherein:
$R^1$, $R^2$, $R^3$, and $R^4$ are as defined in any of the embodiments herein.

According to another embodiment, the present invention provides a compound of formula IB':

wherein X, $R^2$, $R^3$, $R^4$, and Ar are as defined in any of the embodiments herein.

According to another embodiment, the present invention provides a compound of formula IB:

IB wherein:
Ar, $R^1$, $R^2$, $R^3$, and $R^4$ are as defined in any of the embodiments herein.

More specific embodiments of formulae I, IA, IA', IB, and IB' are as defined below.

$R^1$ is an alkyl group that is not substituted with phenyl or $CF_3$. Preferably, $R^1$ is a t-butyl group. Alternatively, $R^1$ is not a t-butyl group. More preferably, $R^1$ is ethyl or propyl.

$R^2$ is ethyl, n-propyl, or isopropyl. More preferably, $R^2$ is ethyl.

Y is F, trifluorophenoxy, or tetrafluorophenoxy.

Ar is 2,3,5,6-tetrafluorophenyl.

$R^3$ is hydrogen and $R^4$ is halo, $OCF_3$, CN, or $CF_3$. Alternatively, $R^3$ is hydrogen and $R^4$ is F, Cl, or $CF_3$. In another embodiment, $R^3$ is hydrogen and $R^4$ is halo. Alternatively, $R^3$ is hydrogen and $R^4$ is chloro.

In one embodiment, X is —$OR^1$. One form of this embodiment provides a compound wherein the $R^1$ of X is an alkyl group that is not substituted with phenyl or $CF_3$. Two other forms of this embodiment are those wherein the alkyl group is substituted with phenyl or $CF_3$. Another form provides a compound wherein the $R^1$ of X is not t-butyl. Yet another form of this embodiment provides a compound wherein the $R^1$ of X is ethyl or propyl.

In another embodiment, X is —$N(R^5)_2$. One form of this embodiment provides a compound wherein one $R^5$ is $C_{1-6}$ straight chained or branched alkyl and the other $R^5$ is —O—$C_{1-6}$ straight chained or branched alkyl. Another form provides a compound wherein one $R^5$ is H or —$C_{1-6}$ straight chained or branched alkyl and the other $R^5$ is —$C_{1-6}$ straight chained or branched alkyl. In any of the embodiments herein, $R^5$ is preferably methyl, ethyl, or propyl.

In one embodiment, if X comprises an aryl, the aryl is optionally substituted phenyl.

In another embodiment, if Y is halo, then both $R^3$ and $R^4$ are not simultaneously hydrogen.

The embodiments herein may be combined to provide a compound according to this invention.

According to a more preferred embodiment, the present invention provides a compound selected from Table 1 below:

TABLE 1

| Example | Structure |
| --- | --- |
| 1 | 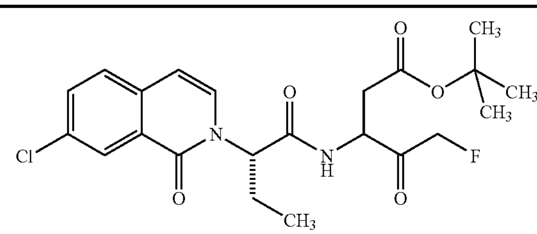 |

TABLE 1-continued

| Example | Structure |
|---|---|
| 2 | (isoquinolin-1(2H)-one with ethyl side chain, amide linked to tert-butyl ester fluoromethyl ketone) |
| 3 | (7-chloroisoquinolin-1(2H)-one with isopropyl side chain, amide linked to tert-butyl ester fluoromethyl ketone) |
| 4 | (isoquinolin-1(2H)-one with propyl side chain, amide linked to tert-butyl ester fluoromethyl ketone) |
| 5 | (7-trifluoromethylisoquinolin-1(2H)-one with ethyl side chain, amide linked to tert-butyl ester fluoromethyl ketone) |
| 6 | (7-chloroisoquinolin-1(2H)-one with ethyl side chain, amide linked to tert-butyl ester with 2,3,5,6-tetrafluorophenoxymethyl ketone) |
| 7 | (7-trifluoromethylisoquinolin-1(2H)-one with ethyl side chain, amide linked to tert-butyl ester with 2,3,5,6-tetrafluorophenoxymethyl ketone) |

TABLE 1-continued

| Example | Structure |
|---|---|
| 8 | 7-chloro-1-oxoisoquinolin-2(1H)-yl-butanoyl-NH-CH(CH2C(O)OEt)-C(O)-CH2F |
| 9 | 7-chloro-1-oxoisoquinolin-2(1H)-yl-butanoyl-NH-CH(CH2C(O)O-n-Pr)-C(O)-CH2F |
| 10 | 7-chloro-1-oxoisoquinolin-2(1H)-yl-butanoyl-NH-CH(CH2C(O)OCH2CH2CF3)-C(O)-CH2F |
| 11 | 7-chloro-1-oxoisoquinolin-2(1H)-yl-butanoyl-NH-CH(CH2C(O)O-i-Pr)-C(O)-CH2F |
| 12 | 7-chloro-1-oxoisoquinolin-2(1H)-yl-butanoyl-NH-CH(CH2C(O)OBn)-C(O)-CH2F |
| 13 | 1-oxoisoquinolin-2(1H)-yl-butanoyl-NH-CH(CH2C(O)O-t-Bu)-C(O)-CH2-O-(2,3,5,6-tetrafluorophenyl) |

TABLE 1-continued

| Example | Structure |
|---|---|
| 14 | 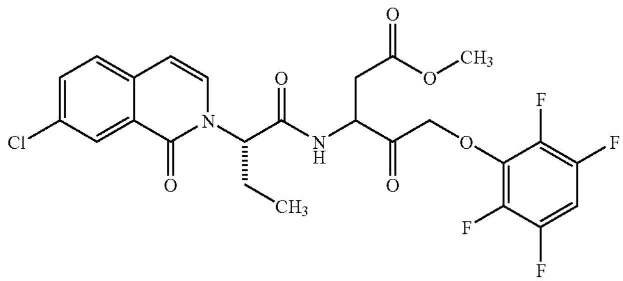 |
| 15 | 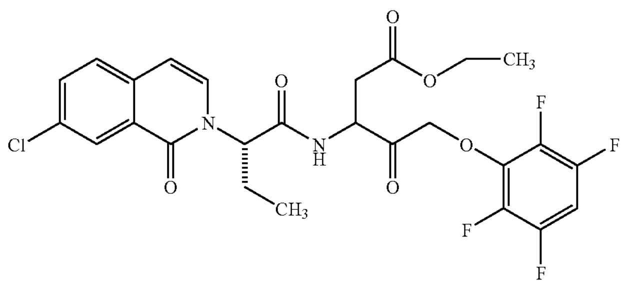 |
| 16 | 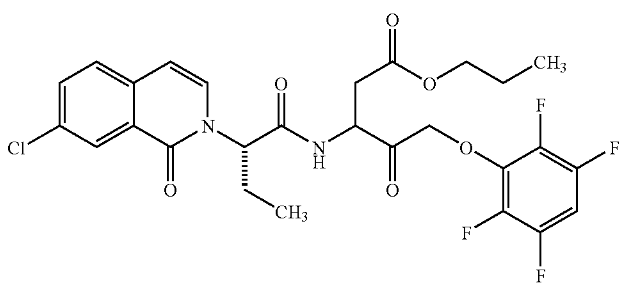 |
| 17 | 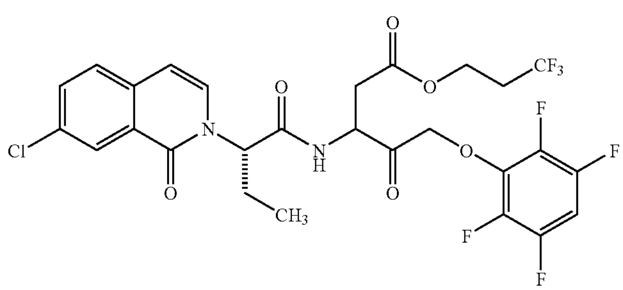 |
| 18 | 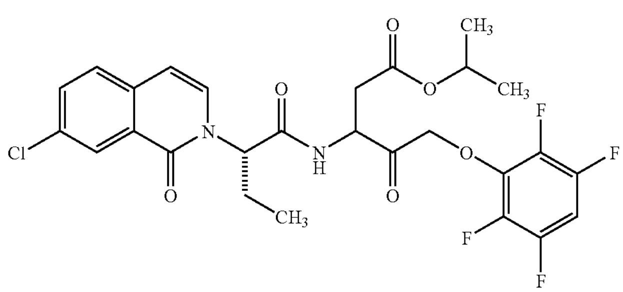 |

TABLE 1-continued

| Example | Structure |
|---|---|
| 19 | 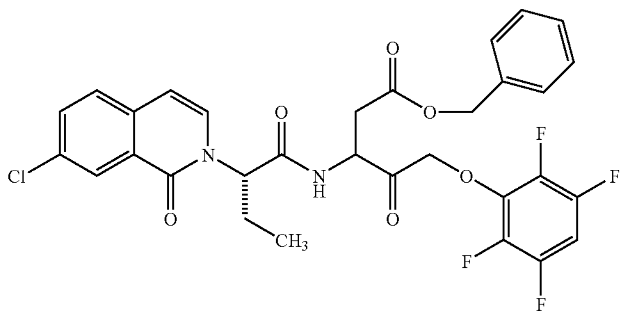 |
| 20 | 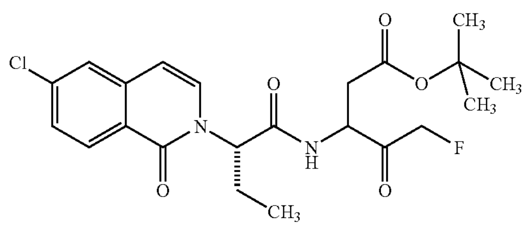 |
| 21 | 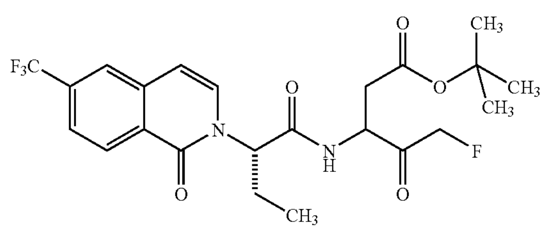 |
| 22 | 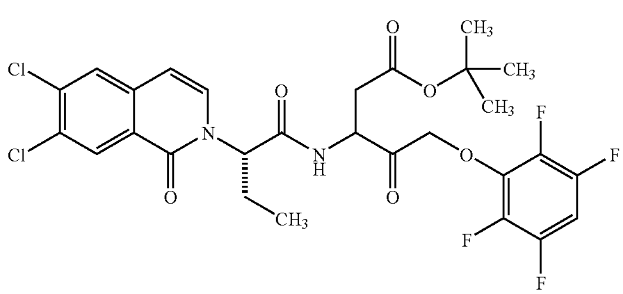 |
| 23 | 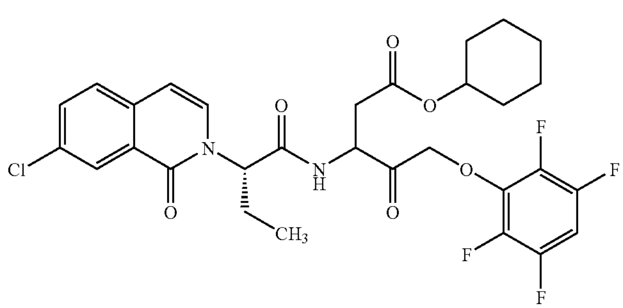 |

TABLE 1-continued

| Example | Structure |
|---|---|
| 24 | 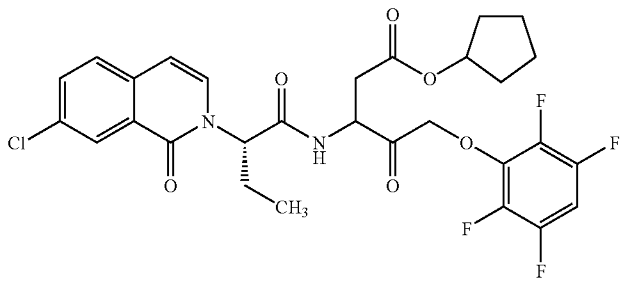 |
| 25 | 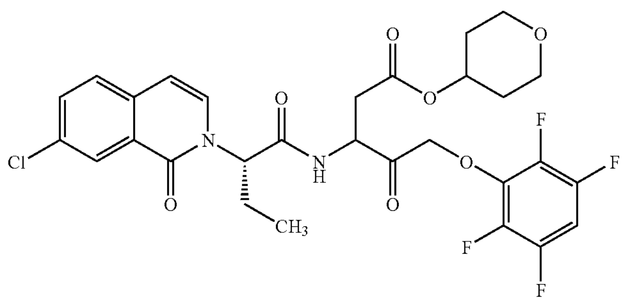 |
| 26 | 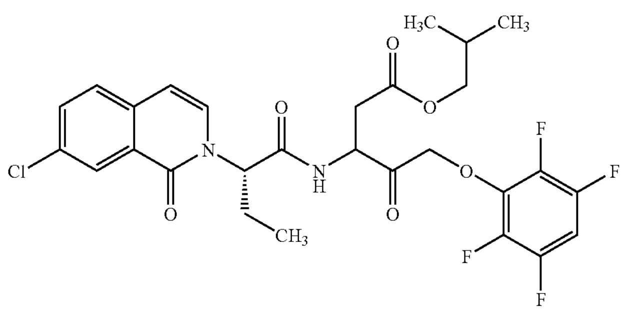 |
| 27 | 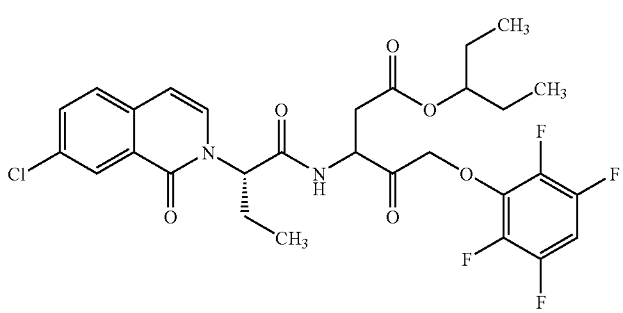 |
| 28 | 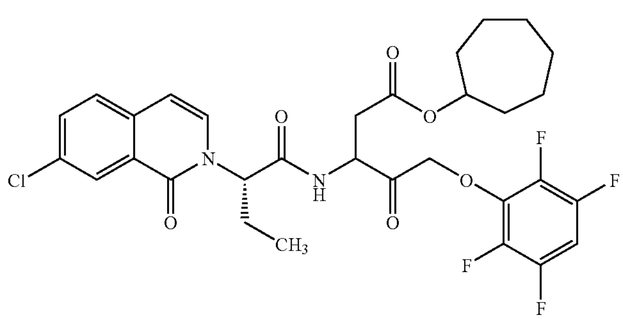 |

TABLE 1-continued

| Example | Structure |
|---|---|
| 29 | 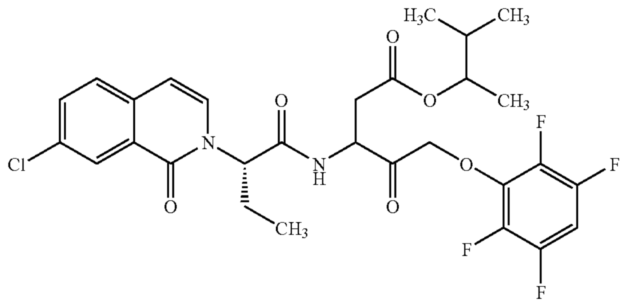 |
| 30 | 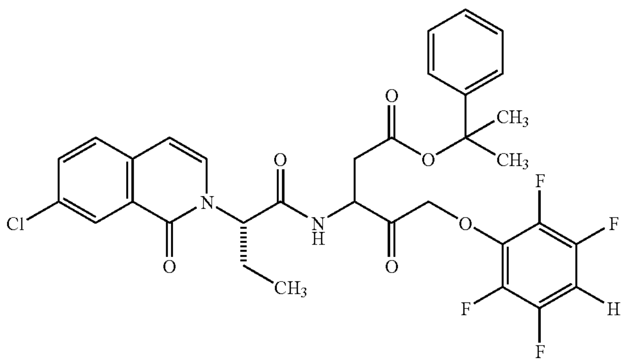 |
| 31 | 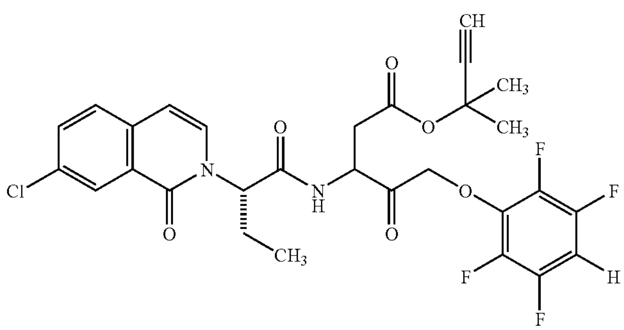 |
| 32 | 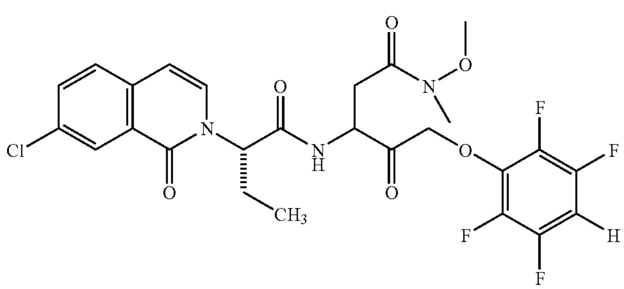 |
| 33 | 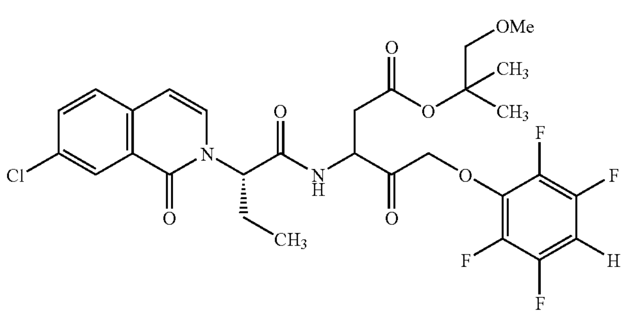 |

TABLE 1-continued

| Example | Structure |
|---|---|
| 34 | 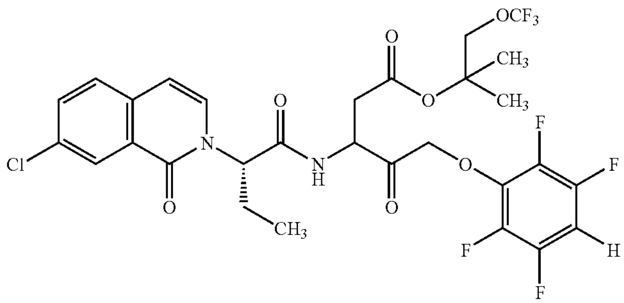 |
| 35 | 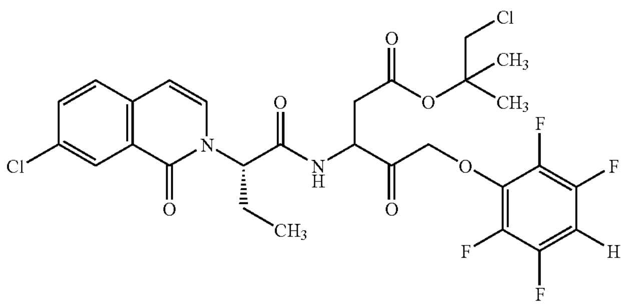 |
| 36 | 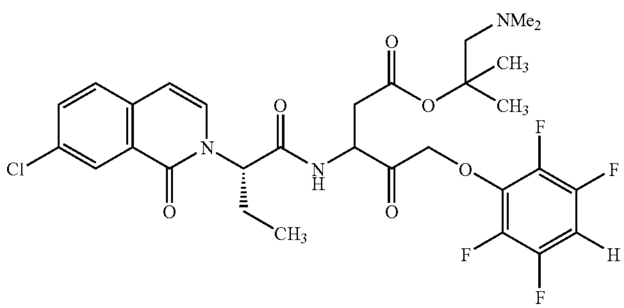 |
| 37 | 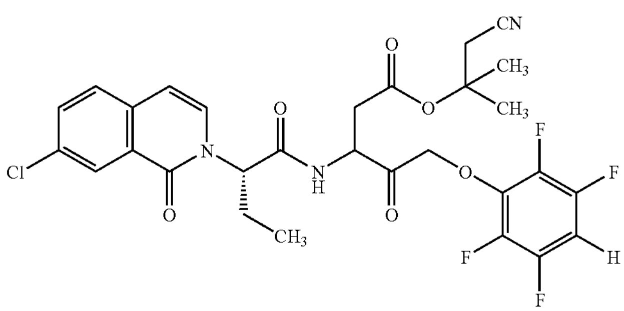 |
| 38 | 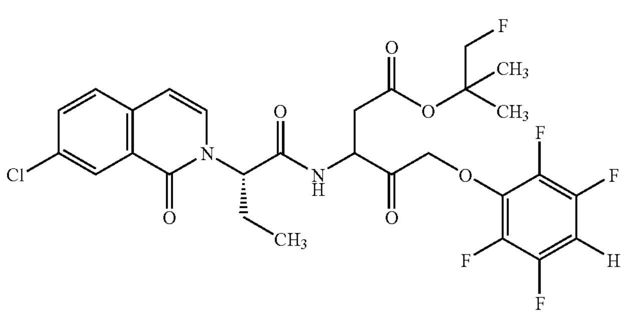 |

TABLE 1-continued

| Example | Structure |
|---|---|
| 39 | 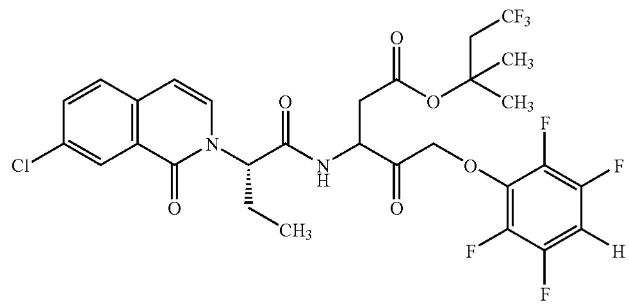 |
| 40 | 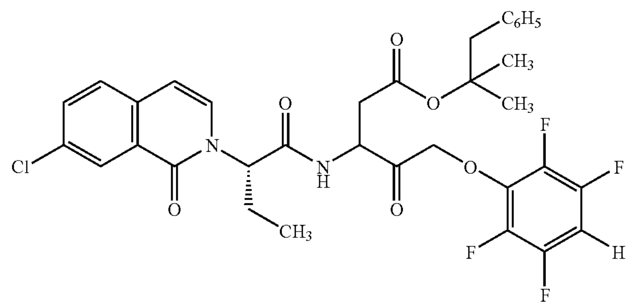 |
| 41 | 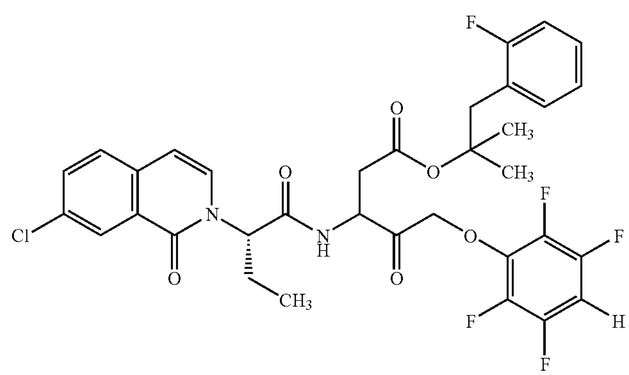 |
| 42 | 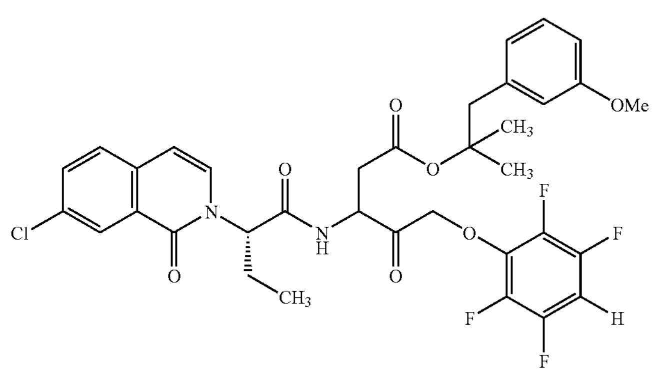 |

TABLE 1-continued

| Example | Structure |
|---|---|
| 43 | 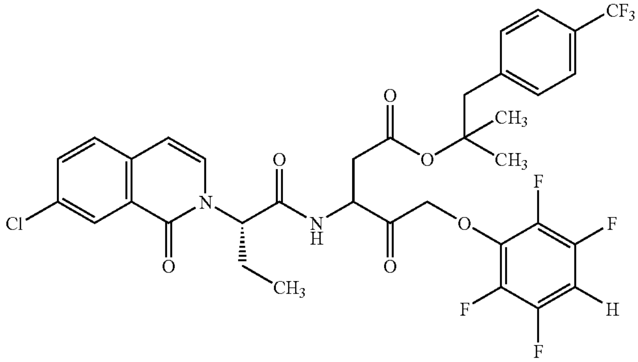 |
| 44 | 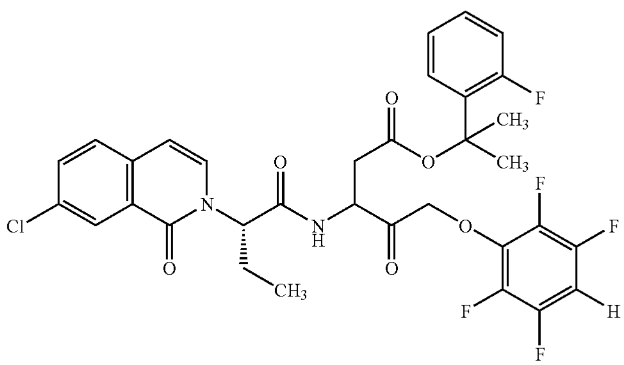 |
| 45 | 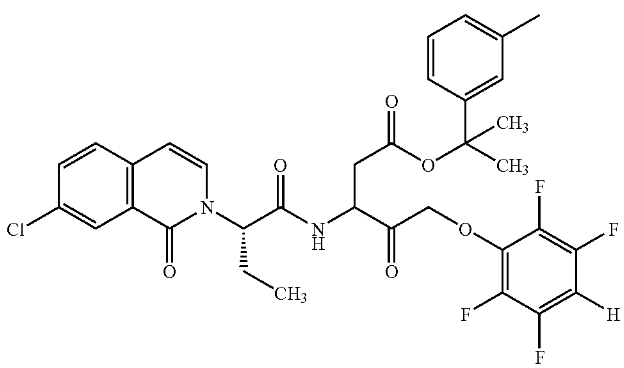 |
| 46 | 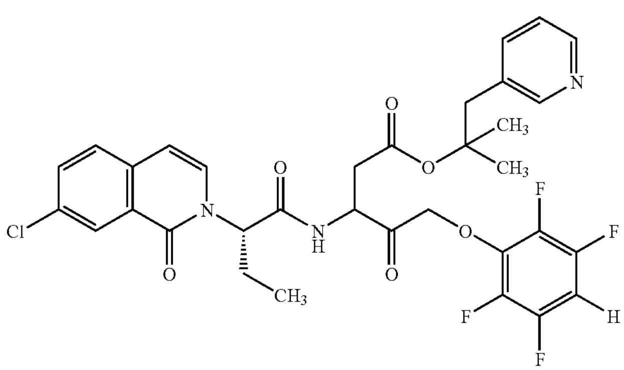 |

TABLE 1-continued

| Example | Structure |
|---|---|
| 47 | 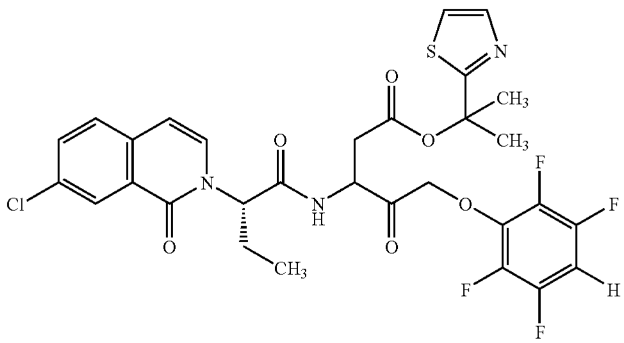 |
| 48 | 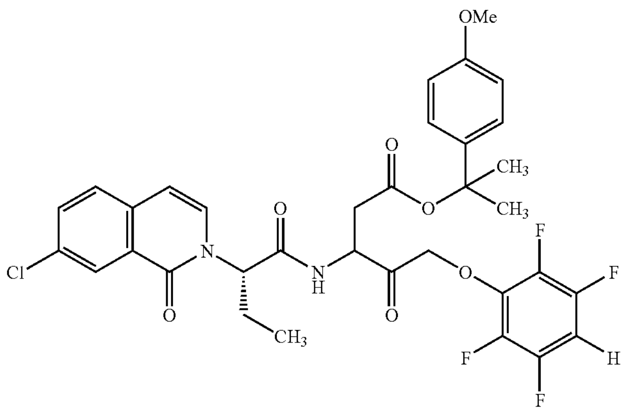 |
| 49 | 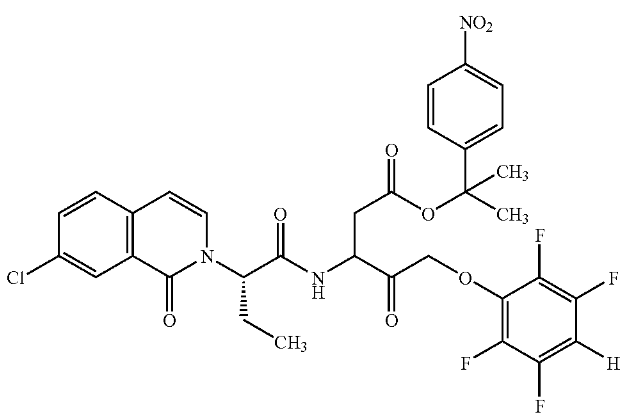 |
| 50 | 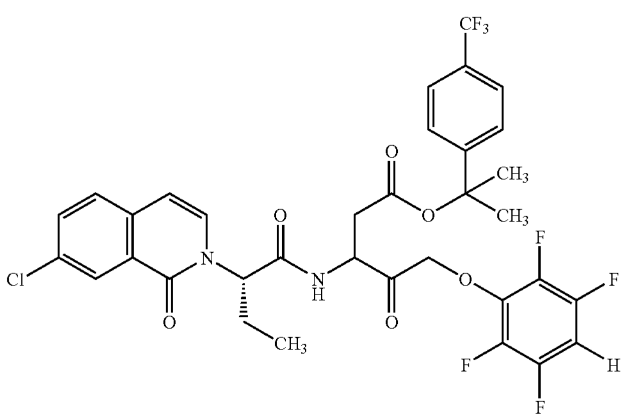 |

TABLE 1-continued
| Example | Structure |
|---|---|
| 51 | 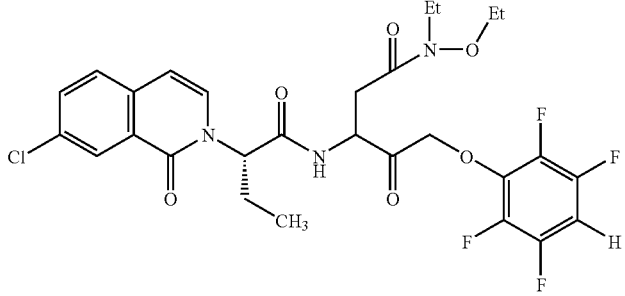 |
| 52 | 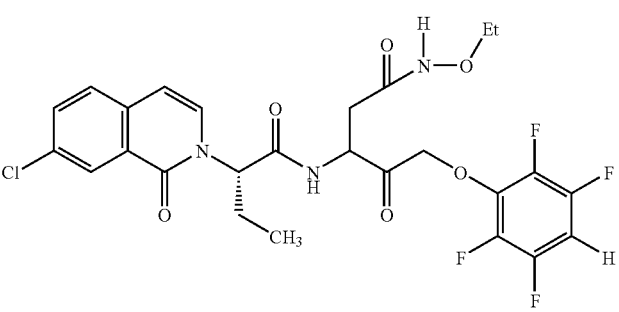 |
| 53 | 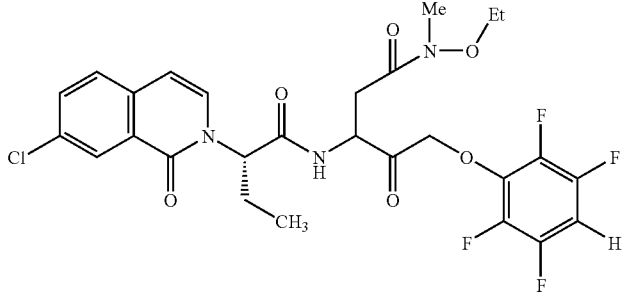 |
| 54 | 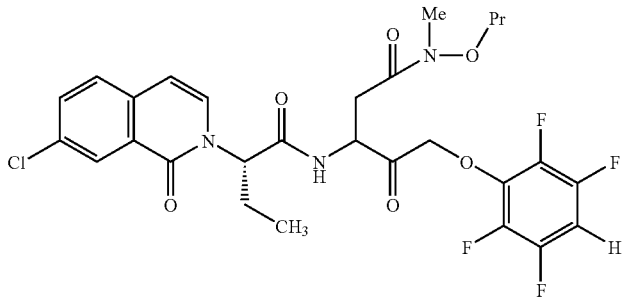 |
| 55 | 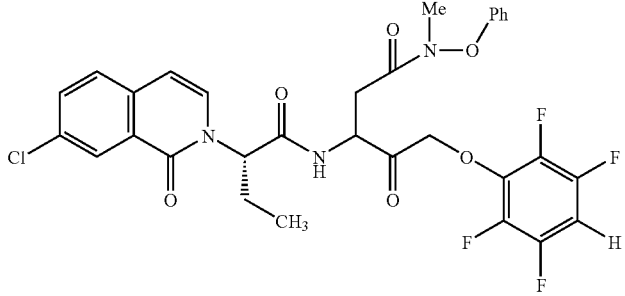 |

TABLE 1-continued
| Example | Structure |
|---|---|
| 56 | 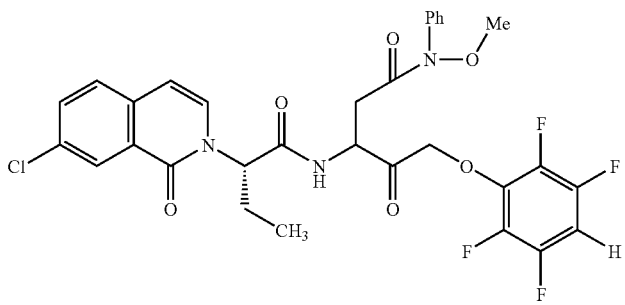 |
| 57 | 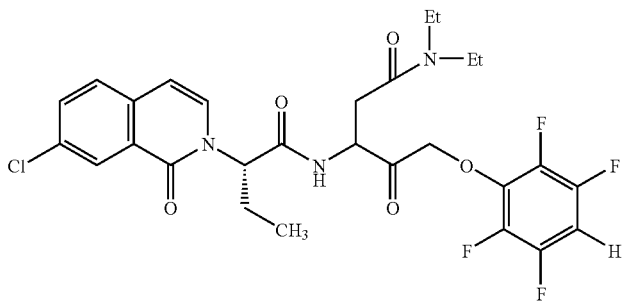 |
| 58 | 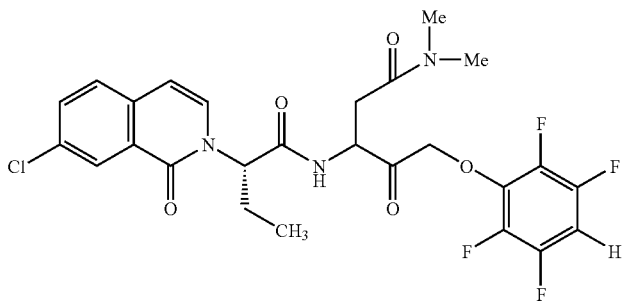 |
| 59 | 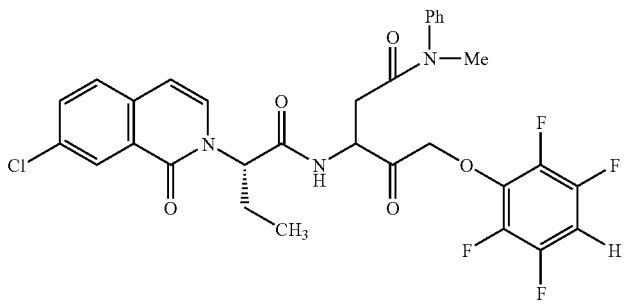 |

TABLE 1-continued

| Example | Structure |
|---|---|
| 60 | *(chemical structure)* |
| 61 | *(chemical structure)* |
| 62 | *(chemical structure)* |

In certain embodiments of this invention, the variables are as defined in the compounds of Table 1.

As used herein, an "aromatic group" or "aryl" refers to a 5-10-membered ring that contains at least one aromatic ring and up to 3 heteroatoms independently selected from N, N($R^7$), O, S, SO, or $SO_2$. Preferred aromatic rings include phenyl, pyridyl, and thiazole.

An aryl group herein is optionally substituted with one or more (preferably 1, 2, or 3) groups selected independently from halogen, —$OR^7$, —OC(O)N($R^7$)$_2$, —$NO_2$, —CN, —$CF_3$, —$OCF_3$, —$R^7$, oxo, thioxo, 1,2-methylenedioxy, 1,2-ethylenedioxy, —N($R^7$)$_2$, —$SR^7$, —$SOR^7$, —$SO_2R^7$, —$SO_2$N ($R^7$)$_2$, —$SO_3R^7$, —C(O)$R^7$, —C(O)C(O) $R^7$, —C(O)CH$_2$C (O) $R^7$, —C(S)$R^7$, —C(O)O$R^7$, —OC(O)$R^7$, —C(O)N($R^7$)$_2$, —OC(O)N($R^7$)$_2$, —C(S)N($R^7$)$_2$, —(CH$_2$)$_{0-2}$NHC(O)$R^7$, —N($R^7$)N($R^7$)CO$R^7$, —N($R^7$)N($R^7$)C(O)O$R^7$, —N($R^7$)N($R^7$) CON($R^7$)$_2$, —N($R^7$) SO$_2R^7$, —N($R^7$) SO$_2$N ($R^7$)$_2$, —N($R^7$)C(O)O$R^7$, —N($R^7$)C(O)$R^7$, —N($R^7$)C(S)$R^7$, —N($R^7$)C(O)N($R^7$)$_2$, —N($R^7$)C(S)N($R^7$)$_2$, —N(CO$R^7$)CO$R^7$, —N(O$R^7$)$R^7$, —C(=NH)N($R^7$)$_2$, —C(O)N(O$R^7$)$R^7$, —C(=NO$R^7$)$R^7$, —OP(O)(O$R^7$)$_2$, —P(O)($R^7$)$_2$, —P(O)(O$R^7$)$_2$, and —P(O)(H)(O$R^7$); wherein $R^7$ is hydrogen-, (C1-C12)-aliphatic-, (C3-C10)-cycloaliphatic-, (C3-C10)-cycloaliphatic]-(C1-C12)-aliphatic-, (C6-C10)-aryl-, (C6-C10)-aryl-(C1-C12)aliphatic-, (C3-C10)-heterocyclyl-, (C6—C10)-heterocyclyl-(C1-C12)aliphatic-, (C5-C10)-heteroaryl-, or (C5-C10)-heteroaryl-(C1-C12)-aliphatic-.

Preferred substituents are independently selected from halogen (particularly F or Cl), alkyl (particularly $CH_3$), fluoroalkyl (particularly $CF_3$), CN, alkoxy (particularly OMe), fluoroalkoxy (particularly $OCF_3$), —$NO_2$, and $N(R^5)_2$ (particularly $NMe_2$).

According to another embodiment, the present invention provides a pharmaceutical composition comprising:

a) a compound of the invention, as defined herein, or a pharmaceutically acceptable salt thereof; and b) a pharmaceutically acceptable carrier, adjuvant or vehicle.

According to a preferred embodiment, the pharmaceutical composition of the present invention comprises:

a) a compound of formula I, IA, IA' IB, or IB'; and b) a pharmaceutically acceptable carrier, adjuvant or vehicle.

According to a more preferred embodiment, the pharmaceutical composition of the present invention comprises a compound selected from Table 1 above.

It will be apparent to one skilled in the art that certain compounds of this invention may exist in tautomeric forms or hydrated forms, all such forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}C$— or $^{14}C$-enriched carbon are within the scope of this invention.

The compounds of this invention may be obtained by any method, including general, synthetic methods known to those skilled in the art for analogous compounds (see e.g., WO 01/42216). For the purposes of illustration, the following Schemes for the synthesis of the compounds of the present invention are provided. The Schemes that depict the preparation of compound wherein X is —$OR^1$ may be modified by routine methods to produce compounds wherein X is —$N(R^5)_2$.

Scheme I

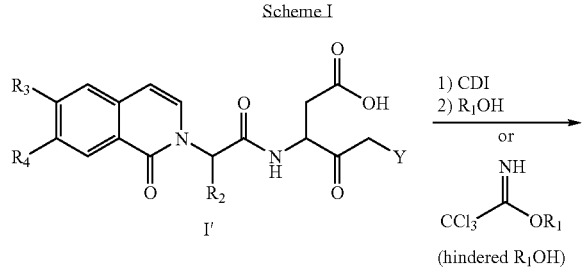

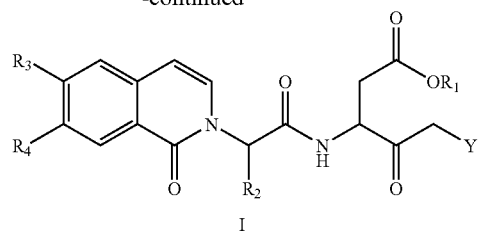

In Scheme I above, the following abbreviations are used: CDI is 1,1'carbonyldiimidazole. Scheme I depicts formation of prodrug esters of formula I. Acid I' is reacted under standard esterification conditions. In Scheme I the conditions depicted include reacting acid I' in the presence of CDI and then in the presence of an appropriate alcohol.

Scheme II

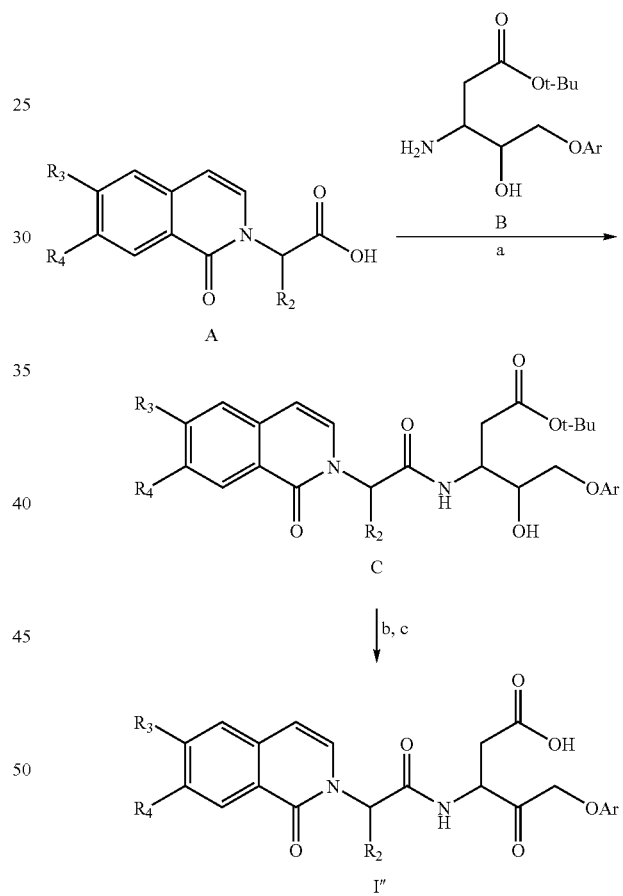

Scheme II (a) EDC/DMAP/HOBt/THF; (b) Dess-Martin periodinane; (c) TFA/DCM.

In Scheme II above, the following abbreviations are used: EDC is 1-(3-dimethylaminopropyl)-3-ethylcarbodiimide; HOBt is 1-hydroxybenzotriazole; THF is tetrahydrofuran; TFA is trifluoroacetic acid; DCM is dichloromethane; DMAP is 4-dimethylaminopyridine. Acid A is coupled to amino alcohol B to provide C. In Scheme II, the coupling conditions depicted involve reacting Acid A and amino alcohol B in the presence of EDC, DMAP, and HOBt in THF. Other acid-amino coupling conditions could be used and would be known to skilled practitioners. In the case of fluoromethyl ketones where CH$_2$OAr is replaced by CH$_2$F, the amino alcohol B may be obtained according to the method of Revesz et al., *Tetrahedron Lett.* 1994, 35, 9693 (which is incorporated herein by reference). In the case of fluoro-substituted phenoxy ketones where Ar is 2,3,5,6-tetrafluorophenoxy, 2,4,6-trifluorophenoxy, or 2,3,6-trifluorophenoxy, the amino alcohol B may be obtained by methods analogous to those of Semple et al., *Bioorganic and Medicinal Chemistry Letters*, 1997, 7, 1337 (Scheme III). C is converted to I" by oxidization under appropriate conditions (e.g., by using Dess-Martin periodinane as depicted here) followed by deprotection under hydrolysis conditions.

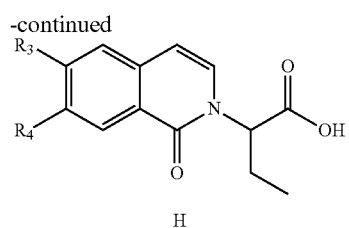

H

Scheme IV (a) heat; (b) cHCl/IPA; (c) TFA/DCM

In Scheme IV the following abreviations are used: IPA is isopropyl alcohol; TFA is trifluoroacetic acid and DCM is

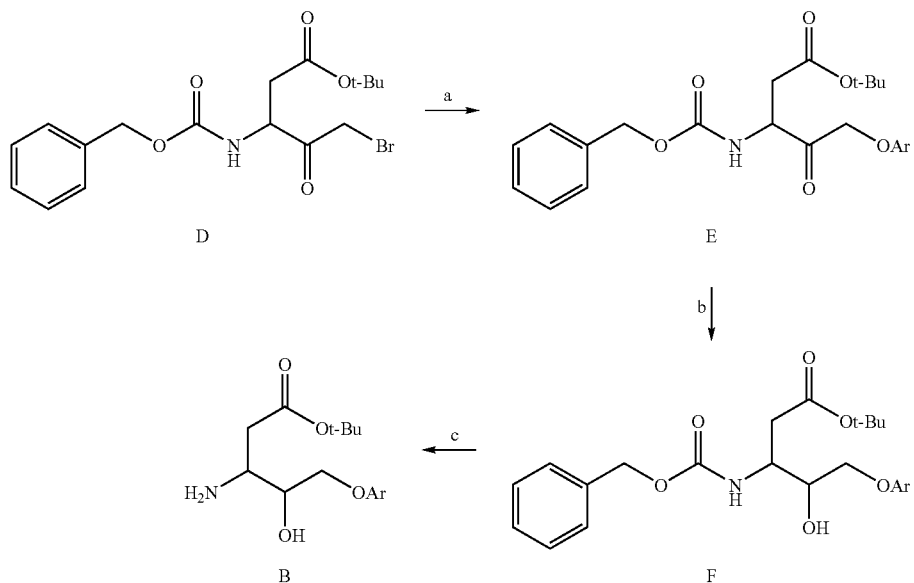

Scheme III (a) KF/DMF/ArOH; (b) NaBH$_4$/THF; (c) H$_2$/Pd/C/MeOH

In scheme III above, the following abbreviations are used: KF is potassium fluoride; DMF is N,N-dimethylformamide; ArOH is either 2,3,5,6-tetrafluorophenol, 2,4,6-trifluorophenol or 2,3,6-trifluorophenol; THF is tetahydrofuran; MeOH is methanol.

Commercially available bromoketone D is reacted with the appropriately substituted fluorophenol and potassium fluoride to give phenoxy ketone E. The ketone is then reduced with sodium borohydride to give the alcohol F, which is hydrogenated using palladium on carbon as catalyst to give the amino alcohol B (in formula I, Y=fluoro-substituted phenoxy).

dichloromethane. Isoquinolin-1-one acid derivatives can be prepared in chiral form using the synthetic sequence shown in Scheme IV. The starting isocoumarin G is prepared by methods analogous to Narasimhan et al. Synthesis 1975, 797 and Margaretha et al. Tetrahedron 2000, 56, 6763 unless stated otherwise. Isocoumarin G is first heated with commercially available (S)-2-aminobutyric acid, tert-butyl ester. The resulting compound is reacted with concentrated hydrochloric acid in isopropanol to give the isoquinolin-1-one tert-butyl ester that is deprotected to provide the acid H using trifluoroacetic acid. The acid is then coupled to amino alcohol B (Scheme II).

Accordingly, this invention also provides a process for preparing a compound of this invention.

One embodiment provides a process for preparing a compound of formula I:

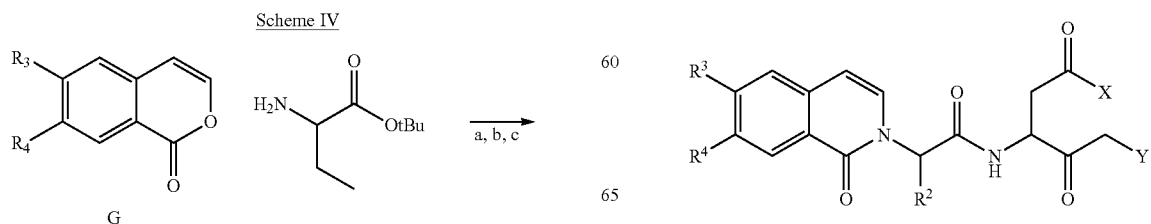

wherein:
    X is —OR¹ or —N(R⁵)₂,
    Y is halo, trifluorophenoxy, or tetrafluorophenoxy;
    R¹ is:
        $C_{1-6}$ straight chained or branched alkyl, alkenyl, or alkynyl, wherein the alkyl, alkenyl, or alkynyl is optionally substituted with aryl, $CF_3$, Cl, F, OMe, OEt, $OCF_3$, CN, or $NMe_2$;
        $C_{1-6}$ cycloalkyl, wherein 1-2 carbon atoms in the cycloalkyl is optionally replaced with —O— or —NR⁵—;
    R² is $C_{1-6}$ straight chained or branched alkyl;
    R³ is hydrogen, halo, $OCF_3$, CN, or $CF_3$;
    R⁴ is hydrogen, halo, $OCF_3$, CN, or $CF_3$; and
        R⁵ is H, $C_{1-6}$ straight chained or branched alkyl, aryl, —O—$C_{1-6}$ straight chained or branched alkyl, or —O-aryl;
    comprising the step of reacting a compound of formula I':

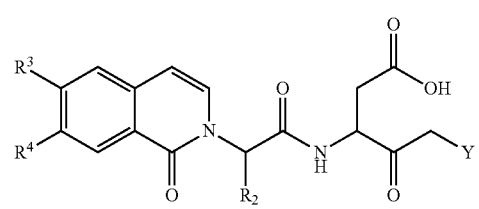

wherein X, Y, R², R³, and R⁴ are as defined for formula I; under conditions forming an ester or amide bond to provide a compound of formula I.

Another embodiment provides a process for preparing a compound of formula I:

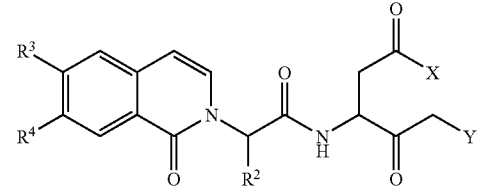

wherein:
    X is —OR¹ or —N(R⁵)₂,
    Y is halo, trifluorophenoxy, or tetrafluorophenoxy;
    R¹ is:
        $C_{1-6}$ straight chained or branched alkyl, alkenyl, or alkynyl, wherein the alkyl, alkenyl, or alkynyl is optionally substituted with aryl, $CF_3$, Cl, F, OMe, OEt, $OCF_3$, CN, or $NMe_2$;
        $C_{1-6}$ cycloalkyl, wherein 1-2 carbon atoms in the cycloalkyl is optionally replaced with —O— or —NR⁵—;
    R² is $C_{1-6}$ straight chained or branched alkyl;
    R³ is hydrogen, halo, $OCF_3$, CN, or $CF_3$;
    R⁴ is hydrogen, halo, $OCF_3$, CN, or $CF_3$; and R⁵ is H, $C_{1-6}$ straight chained or branched alkyl, aryl, —O—$C_{1-6}$ straight chained or branched alkyl, or —O-aryl;
comprising the step of coupling a compound of formula A and a compound of formula K:

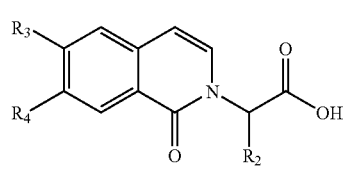

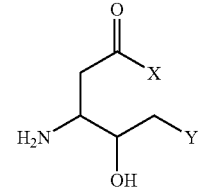

to provide a compound of formula L:

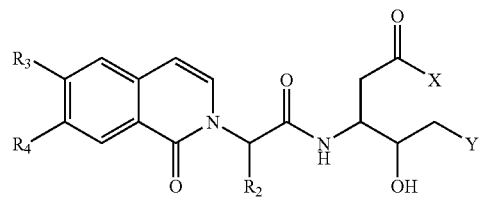

wherein X, Y, R¹, R², R³, and R⁴ are as defined in formula I and wherein the hydroxy group in K is optionally protected.

Another embodiment provides a process for preparing a compound of formula I:

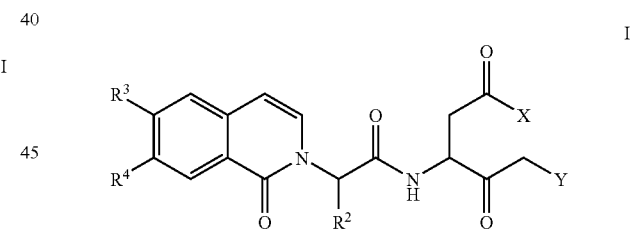

wherein:
    X is —OR¹ or —N(R⁵)₂,
    Y is halo, trifluorophenoxy, or tetrafluorophenoxy;
    R¹ is:
        $C_{1-6}$ straight chained or branched alkyl, alkenyl, or alkynyl, wherein the alkyl, alkenyl, or alkynyl is optionally substituted with aryl, $CF_3$, Cl, F, OMe, OEt, $OCF_3$, CN, or $NMe_2$;
        $C_{1-6}$ cycloalkyl, wherein 1-2 carbon atoms in the cycloalkyl is optionally replaced with —O— or —NR⁵—;
    R² is $C_{1-6}$ straight chained or branched alkyl;
    R³ is hydrogen, halo, $OCF_3$, CN, or $CF_3$;
    R⁴ is hydrogen, halo, $OCF_3$, CN, or $CF_3$; and
        R⁵ is H, $C_{1-6}$ straight chained or branched alkyl, aryl, —O—$C_{1-6}$ straight chained or branched alkyl, or —O-aryl;
    comprising the step of oxidizing a compound of formula L:

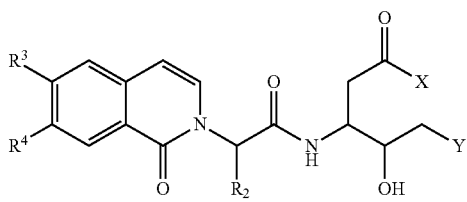

wherein X, Y, R¹, R², R³, and R⁴ are as defined for formula I; to provide a compound of formula I.

In preferred embodiments, the above processes are as described herein (e.g., in the schemes, examples, and accompanying description).

The compounds of this invention may be assayed for their ability to inhibit apoptosis, the release of IL-1β or caspase activity directly. Assays for each of the activities are known in the art. However, as would be recognized by a skilled practitioner, the prodrug compounds of this invention should be active only in assays where the prodrug moiety would be cleaved, typically in in vivo assays.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The above-described compositions are particularly useful in therapeutic applications relating to an IL-1 mediated disease, an apoptosis mediated disease, an inflammatory disease, an autoimmune disease, a destructive bone disorder, a proliferative disorder, an infectious disease, a degenerative disease, a disease associated with cell death, an excess dietary alcohol intake disease, a viral mediated disease, retinal disorders, uveitis, inflammatory peritonitis, osteoarthritis, pancreatitis, asthma, adult respiratory distress syndrome, glomerulonephritis, rheumatoid arthritis, systemic lupus erythematosus, scleroderma, chronic thyroiditis, Grave's disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, scarring, graft vs host disease, organ transplant rejection, organ apoptosis after burn injury, osteoporosis, leukemias and related disorders, myelodysplastic syndrome, multiple myeloma-related bone disorder, acute myelogenous leukemia, chronic myelogenous leukemia, metastatic melanoma, Kaposi's sarcoma, multiple myeloma, hemorrhagic shock, sepsis, septic shock, burns, Shigellosis, Alzheimer's disease, Parkinson's disease, Huntington's disease, Kennedy's disease, prion disease, cerebral ischemia, epilepsy, myocardial ischemia, acute and chronic heart disease, myocardial infarction, congestive heart failure, atherosclerosis, coronary artery bypass graft, spinal muscular atrophy, amyotrophic lateral sclerosis, multiple sclerosis, HIV-related encephalitis, aging, alopecia, neurological damage due to stroke, ulcerative colitis, traumatic brain injury, spinal cord injury, hepatitis-B, hepatitis-C, hepatitis-G, yellow fever, dengue fever, Japanese encephalitis, various forms of liver disease, renal disease, polycystic kidney disease, *H. pylori*-associated gastric and duodenal ulcer disease, HIV infection, tuberculosis, and meningitis. The compounds and compositions are also useful in treating complications associated with coronary artery bypass grafts. The compounds and compositions are also useful for decreasing TGIF or IFN-γ production. The compounds and compositions are also useful in immunotherapy as a cancer treatment.

The compounds and compositions of this invention are particularly useful in therapeutic applications relating to inhibition of caspase activity in the central nervous system and/or the brain. These applications include treating neurological damage due to stroke, traumatic brain injury, and spinal cord injury.

The compounds and compositions may also be used in methods for preserving cells. These methods would be useful for preserving organs, particularly those intended for transplant, or blood products.

According to another embodiment, the compositions of this invention may further comprise another therapeutic agent. Such agents include, but are not limited to, thrombolytic agents such as tissue plasminogen activator and streptokinase. When a second agent is used, the second agent may be administered either as a separate dosage form or as part of a single dosage form with the compounds or compositions of this invention.

The amount of compound present in the compositions of this invention should be sufficient to cause a detectable decrease in the severity of the disease or in caspase activity and/or cell apoptosis, as measured by any of the assays known in the art.

Dosage levels of between about 0.01 and about 50 or about 100 mg/kg body weight per day, preferably between 0.5 and about 75 mg/kg body weight per day and most preferably between about 1 and about 25 or about 50 mg/kg body weight per day of the active ingredient compound are useful in a monotherapy.

Typically, a compound or composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of this invention and one or more additional therapeutic or prophylactic agents, both the compound and the additional agent should be present at dosage levels of between about 10% to about 100%, and more preferably between about 10% to about 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease.

Patients may, however, require intermittent treatment on a long-term basis upon any recurrence of disease symptoms.

As the skilled practitioner will appreciate, lower or higher doses than those recited above may be required. It should be understood that a specific dosage and treatment regimens for any particular patient will depend upon a variety of factors, including the activity of the specific compound employed, the age, body weight, general health, sex, diet, time of administration, rate of excretion, drug combination, the severity and course of the particular disease, the patient's disposition to the disease being treated, and the judgment of the treating physician. The amount of active ingredients will also depend upon the particular compound and other therapeutic agent, if present, in the composition.

In a preferred embodiment, the invention provides a method of treating a patient, preferably a mammal, having one of the aforementioned diseases, comprising the step of administering to said patient a compound or a pharmaceutically acceptable composition described above. In this embodiment, if the patient is also administered another therapeutic agent or caspase inhibitor, it may be delivered together with the compound of this invention in a single dosage form, or, as a separate dosage form. When administered as a separate dosage form, the other caspase inhibitor or agent may be administered prior to, at the same time as, or following administration of a pharmaceutically acceptable composition comprising a compound of this invention.

The compounds of this invention may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention and a carrier suitable for coating said implantable device. In still another aspect, the present invention includes an implantable device coated with a composition comprising a compound of the present invention and a carrier suitable for coating said implantable device.

Another aspect of the invention relates to inhibiting caspase activity in a biological sample, which method comprises contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of caspase activity in a biological sample is useful for a variety of purposes that are known to one of skill in the art. Examples of such purposes include, but are not limited to, blood transfusion, organ-transplantation, biological specimen storage, and biological assays.

The compounds of this invention are useful in methods for preserving cells, such as may be needed for an organ transplant or for preserving blood products. Similar uses for caspase inhibitors have been reported (Schierle et al., *Nature Medicine*, 5, 97 (1999)). The method involves treating the cells or tissue to be preserved with a solution comprising the caspase inhibitor. The amount of caspase inhibitor needed will depend on the effectiveness of the inhibitor for the given cell type and the length of time required to preserve the cells from apoptotic cell death.

Nevertheless, the compounds of this invention are particularly suitable for methods involving inhibition of caspase activity in the central nervous system. Without being bound by theory, applicants' ester, amide-, and hydroxamide-containing prodrugs have the ability to pass through the blood brain barrier and into the central nervous system where the prodrug group is cleaved to provide an acid-containing drug. As would be recognized by a skilled practitioner, chemical compounds may be metabolized in vivo (i.e., at sites other than the prodrug cleavage site). Any such metabolites are included within the scope of this invention.

In order that this invention be more fully understood, the following preparative and testing examples are set forth. These examples are for the purpose of illustration only and are not to be construed as limiting the scope of the invention in any way.

EXAMPLE 1

S-3-[2-(7-chloro-1-oxo-1H-isoquinolin-2-yl)-butyrylamino]-5-fluoro-4-oxo-pentanoic acid tert butyl ester

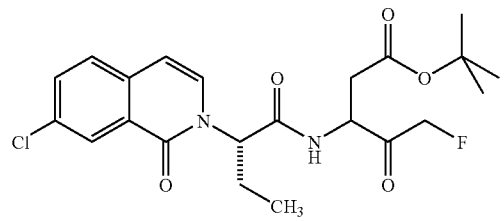

Method A:

5-Chloro-2(2-methoxyvinyl)-benzoic acid

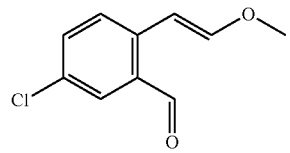

To a cooled (0° C.) slurry of methoxymethyltriphenylphosphonium chloride (39 g) in a mixture of diethyl ether (200 ml) and tert-butanol (50 ml) was added potassium tert-butoxide (12.8 g) portionwise. The resulting mixture was stirred at 0° C. for 1 hour, then a solution of 2-formyl-5-chlorobenzoic acid (prepared as described in J. Org. Chem. 1996, 61, 3402) (10 g) in diethyl ether (50 ml) was added dropwise over 15 minutes. The resulting mixture was stirred for 1 hour at 0° C., then warmed to ambient and stirred for an additional 90 minutes. The mixture was diluted with water (200 ml) and the organic phase removed. The aqueous phase was acidified to pH1 with 1M HCl and extracted with ethyl acetate (3×50 ml). The combined extracts were washed with brine, dried (magnesium sulfate), filtered and concentrated. The residue was purified by flash chromatography (50% ethyl acetate/hexane) to afford the sub-title compound as a yellow solid (9.13 g, 80%): $^1$H NMR (400 MHz, CDCl$_3$) δ 3.70-3.81 (3H, s), 6.20 (0.3 H, d), 6.30 (0.3 H, d), 6.80 (0.7 H, d), 7.01 (0.7 H, d), 7.30-8.15 (3H, m).

Method B:

7-Chloro-isochromen-1-one

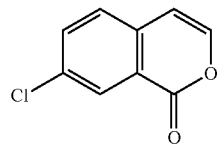

Concentrated sulphuric acid (15 ml) was added to 5-chloro-2(2-methoxyvinyl)-benzoic acid (4.43 g) at 0° C. The mixture was stirred for 2 hours, then diluted with ice/water. The product was extracted with ethyl acetate (3×15 ml) and the combined extracts washed with saturated sodium bicarbonate solution. The solution was dried (magnesium sulfate), filtered and concentrated. The residue was purified by flash chromatography (0-5% ethyl acetate/hexane) to afford the sub-title compound as a white solid (3.04 g, 81%); mp 109.8-110.9° C.; $^1$H NMR (400 MHz, CDCl$_3$) δ 6.51 (1H, d), 7.28-7.32 (1H, m), 7.41 (1H, d), 7.64-7.70 (1H, m), 8.28 (1H, m).

Method C:

2-[3-(1-tertButoxycarbonyl-propylamino)-7-chloro-1-oxo-3,4-dihydro-1H-isoquinolin-2-yl]-butyric acid tert-butyl ester

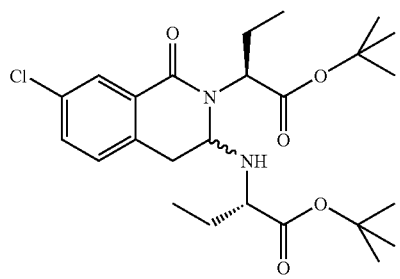

A mixture of 7-Chloro-isochromen-1-one (10 g) and (S)-2-aminobutyric acid, tert-butyl ester (22 g) was heated at 85° C. for 24 hours. The mixture was then cooled and purified by flash chromatography (5-25% ethyl acetate/hexane) to afford the sub-title compound as a yellow oil (17.1 g, 64%): $^1$H NMR (400 MHz, CDCl$_3$) δ 0.68-1.32 (6H, m), 1.50 (21H, m), 1.92 (1H, m), 2.15 (1H, m), 2.82-3.40 (3H, m), 4.41 (1H, m), 4.68 (1H, m), 7.11 (1H, m), 7.35-7.52 (1H, m), 8.05 (1H, m).

Method D:

(S)-2-(7-Chloro-1-oxo-1H-isoquinolin-2-yl)-butyric acid, tert butyl ester

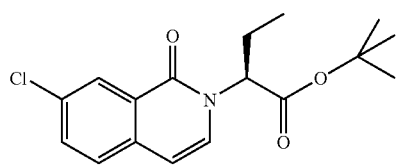

To a stirred solution of 2-[3-(1-tertbutoxycarbonyl-propylamino)-7-chloro-1-oxo-3,4-dihydro-1H-isoquinolin-2-yl]-butyric acid tert-butyl ester (8.58 g) in isopropanol (180 ml) at 0° C. was added concentrated hydrochloric acid (20 ml). The resulting mixture was allowed to warm to ambient and stirred for 18 hours. The mixture was then diluted with ethyl acetate (500 ml) and water (150 ml). The organic phase was separated and washed with water, then brine, dried (magnesium sulfate), filtered and concentrated. The sub-title product was obtained as a yellow solid (5.57 g, 97%); m.p. 111.3-111.8° C.; $[\alpha]^{25}_D$-52.3° (c=1, CDCl$_3$); IR (solid) 1731.4, 1649.5, 1593.2, 1229.6, 1152.8, 901.9 cm$^{-1}$; $^1$H NMR (400 MHz, CDCl$_3$) δ 0.95 (3H, t), 1.48 (9H, s), 1.95 (1H, m), 2.30 (1H, m), 5.55 (1H, m), 6.40 (1H, m), 7.15 (1H, m), 7.49 (1H, m), 7.61 (1H, m), 8.40 (1H, m); $^{13}$C NMR (100 MHz, CDCl$_3$) δ 10.9, 24.8, 28.1, 59.2, 82.8, 105.7, 127.3, 127.8, 128.1, 129.5, 133.1, 133.2, 135.4, 161.8, 170.2; MS ES(+) 322.4 (M+H).

Method E:

(S)-2-(7-Chloro-1-oxo-1H-isoquinolin-2-yl)-butyric acid

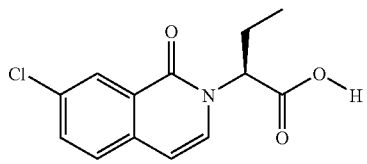

A solution of (S)-2-(7-Chloro-1-oxo-1H-isoquinolin-2-yl)-butyric acid, tert butyl ester (322 mg) in dichloromethane (14 ml) was cooled to 0° C. Trifluoroacetic acid (3.5 ml) was added and the resulting mixture allowed to warm to room temperature and stir for 2 hours. The mixture was then concentrated under reduced pressure and the residue redissolved in dichloromethane. This process was repeated several times in order to remove excess trifluoroacetic acid. The resulting solid was slurried in diethyl ether, filtered and washed with more diethyl ether. The solid was then dried to constant weight under vacuum. This gave the sub-title product as a white solid (236 mg, 89%); m.p. 159.6-160.1° C.; $[\alpha]^{24}_D$-47.0° (c=1.01, CDCl$_3$); it (solid) 1731.4, 1639.3, 1577.8, 1209.1, 1168.1 cm$^{-1}$; $^1$H NMR (400 MHz, d6-DMSO) δ 0.82 (3H, t), 2.00-2.25 (2H, m), 5.20 (1H, m), 6.70 (1H, d), 7.49 (1H, d), 7.70-7.81 (2H, m), 8.18 (1H, s); $^{13}$C NMR (100 MHz, d6-DMSO) δ 10.8, 22.7, 60.8, 104.9, 126.5, 126.6, 128.8, 131.6, 132.5, 133.1, 135.8, 160.5, 171.7; MS ES (+) 266.27 (M+H).

Method F:

3-[2-(7-Chloro-1-oxo-1H-isoquin-2-yl)-butyrylamino]-5-fluoro-4-hydroxy-pentanoic acid tert butyl ester

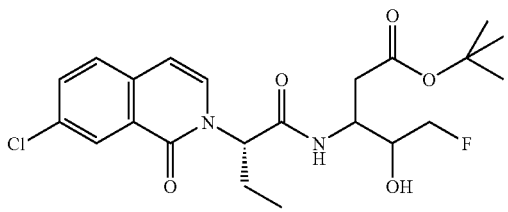

A stirred mixture of (S)-2-(7-chloro-1-oxo-1H-isoquinolin-2-yl)-butyric acid (15 g), 3-amino-5-fluoro-4-hydroxypentanoic acid tert-butyl ester (prepared as described in *Tetrahedron Lett.* 1994, 35, 9693) (12.9 g), HOBt (8.4 g), DMAP (7.2 g) and THF (450 ml) was cooled to 0° C. then EDC (11.9 g) was added. The mixture was allowed to warm to room temperature during 16 h then concentrated under reduced pressure. The residue was purified by flash chromatography (30-60% ethyl acetate/hexane) to afford the subtitle compound as a white foam (24.6 g, 96%); $^1$H NMR (400 MHz, CDCl$_3$) δ 0.92 (3H, m), 1.13-1.50 (9H, m), 1.95 (1H, m), 2.25 (1H, m), 2.45-2.78 (2H, m), 3.68-4.60 (5H, m), 5.50 (1H, m), 6.60 (1H, m), 7.21-7.60 (4H, m), 8.20-8.31 (1H, m); $^{19}$F NMR (376 MHz, CDCl$_3$) (proton decoupled) δ -229.6, -229.7, -230.5, -230.6.

Method G:

3-[2-(7-Chloro-1-oxo-1H-isoquin-2-yl)-butyrylamino]-5-fluoro-4-oxo-pentanoic acid tert butyl ester

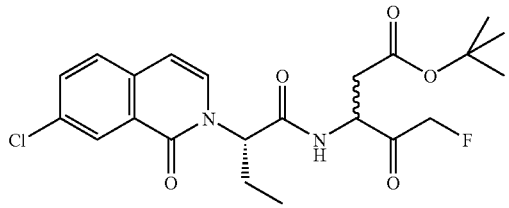

A stirred solution of 3-[2-(7-chloro-1-oxo-1H-isoquin-2-yl)-butyrylamino]-5-fluoro-4-hydroxy-pentanoic acid tert butyl ester (47.8 g) in anhydrous DCM (1.2L) was treated with 1,1,1-triacetoxy-1,1-dihydro-1,2-benziodoxol-3(1H)-one (53.5 g) at 0° C. The resulting mixture was kept at 0° C. for 2 hr, diluted with ethyl acetate, then poured into a 1:1 mixture of saturated aqueous sodium hydrogen carbonate and saturated aqueous sodium thiosulfate. The organic layer was removed and the aqueous layer re-extracted with ethyl acetate. The combined organic extracts were dried (Magnesium sulfate), filtered and concentrated. The residue was purified by flash chromatography (20-40% ethyl acetate/hexane) to afford the subtitle compound as a white solid (41.9 g, 88%); $^1$H NMR (400 MHz, CDCl$_3$) δ 1.00 (3H, t), 1.29 (5H, s), 1.41 (4H, s), 2.01 (1H, m), 2.29 (1H, m), 2.61-3.05 (2H, m), 4.77 (3H, m), 5.50 (1H, m), 6.60 (1H, m), 7.20-7.34 (2H, m), 7.51 (1H, m), 7.62 (1H, m), 8.41 (1H, m); $^{19}$F NMR (376 MHz, CDCl$_3$)(proton decoupled) δ -231.89, -232.30; ES(+) 453.1, ES(-) 451.1.

EXAMPLE 2

S-3-[2-(1-oxo-1H-isoquinolin-2-yl)-butyrylamino]-5-fluoro-4-oxo-pentanoic acid tert butyl ester

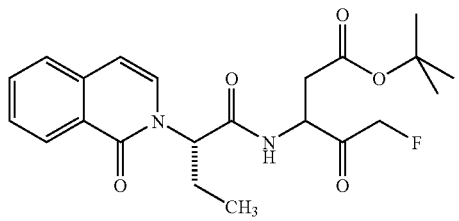

This compound was prepared using methods similar to A-G and was isolated as a white foam.

$^1$H NMR (400 MHz, CDCl$_3$) δ 1.10 (3H, m), 1.31 (5H, s), 1.45 (4H, s), 2.02 (1H, m), 2.31 (1H, m), 2.60-2.82 (1H, m), 2.88-3.08 (1H, m), 4.75-5.28 (3H, m), 5.51 (1H, m), 6.60 (1H, m), 7.20-7.40 (2H, m), 7.60 (2H, m), 7.71 (1H, m), 8.42 (1H, m); $^{19}$F NMR (376 MHz, CDCl$_3$) (proton decoupled) δ -232.0, -232.5; ES(+) 419.3, ES(-) 417.3.

EXAMPLE 3

S-3-[2-(7-chloro-1-oxo-1H-isoquinolin-2-yl)-3-methylbutyrylamino]-5-fluoro-4-oxo-pentanoic acid tert butyl ester

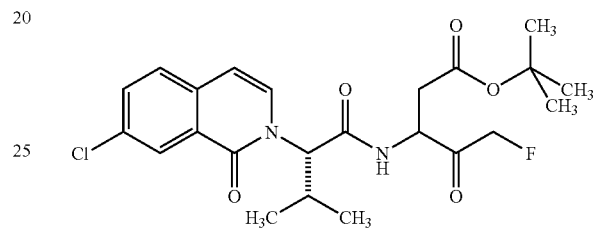

This compound was prepared using methods similar to A-G and was isolated as a white foam $^1$H NMR (400 MHz, CDCl$_3$) δ 0.83 (3H, m), 1.13 (3H, m), 1.30 (4.5H, s), 1.43 (4.5H, s), 2.55 (1H, m), 2.66-3.00 (2H, m), 4.74-5.30 (4H, m), 6.55 (1H, d), 7.32-7.62 (4H, m), 8.35 (1H, d); $^{19}$F NMR (376 MHz, CDCl$_3$) (proton decoupled) δ -231.5, -232.1; ES(+) 467.4.

EXAMPLE 4

S-3-[2-(1-oxo-1H-isoquinolin-2-yl)-valerylamino]-5-fluoro-4-oxo-pentanoic acid tert butyl ester

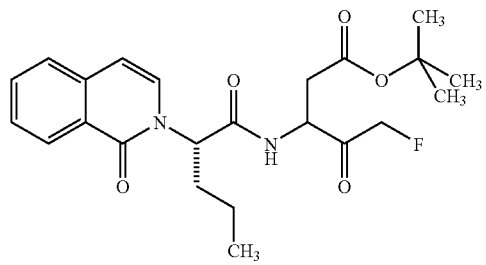

This compound was prepared using methods similar to A-G and was isolated as a white solid $^1$H NMR (400 MHz, CDCl$_3$) δ 1.01 (3H, m), 1.15-1.46 (11H, m), 1.98 (1H, m), 2.22 (1H, m), 2.60-3.04 (2H, m), 4.71-5.31 (3H, m), 5.61 (1H, m), 6.60 (1H, m), 7.18-7.30 (2H, m), 7.52 (2H, m), 7.70 (1H, m), 8.40 (1H, m); $^{19}$F NMR (376 MHz, CDCl$_3$) (proton decoupled) δ −232.0, −232.5; ES(+) 433.5, ES(−) 431.5.

EXAMPLE 5

S-3-[2-(7-trifluoromethyl-1-oxo-1H-isoquinolin-2-yl)-butyrylamino]-5-fluoro-4-oxo-pentanoic acid tert butyl ester

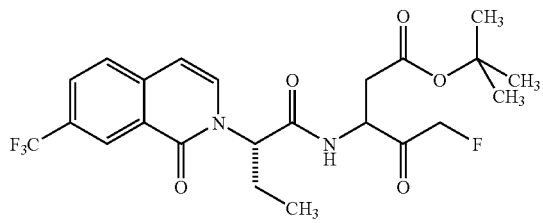

This compound was prepared using methods similar to A-G and was isolated as a white solid
$^1$H NMR (400 MHz, CDCl$_3$) δ 1.01 (3H, m), 1.20-1.40 (9H, 2s), 2.00 (1H, m), 2.30 (1H, m), 2.60-3.05 (2H, m), 4.75-5.26 (3H, m), 5.48 (1H, m), 6.62 (1H, m), 7.22 (1H, brs), 7.62 (1H, m), 7.65 (1H, m), 8.82 (1H, m), 8.65-8.72 (1H, m); $^{19}$F NMR (376 MHz, CDCl$_3$) (proton decoupled) δ −62.85, −62.88, −231.85, −232.20; ES(+) 487.5, ES(−) 485.5.

EXAMPLE 6

S-3-[2-(7-chloro-1-oxo-1H-isoquinolin-2-yl)-butyrylamino]-4-oxo-5-(2,3,5,6-tetrafluoro-phenoxy)-pentanoic acid tert butyl ester

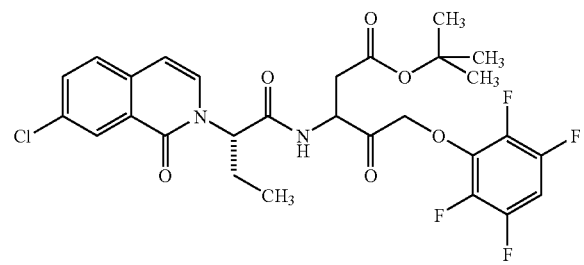

Method H:

(S)-3-Benzyloxycarbonylamino-4-oxo-5-(2,3,5,6-tetrafluoro-phenoxy)-pentanoic acid tert-butyl ester

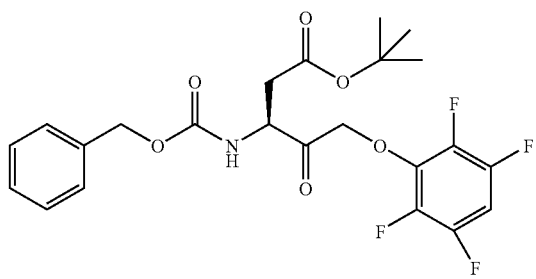

Potassium fluoride (2.8 g), was added portionwise to a stirred solution of (S)-3-benzyloxycarbonylamino-5-bromo-4-oxo-pentanoic acid tert-butyl ester (18.6 g) and 2,3,5,6-tetrafluorophenol (9.3 g) in anhydrous DMF (250 mL) under nitrogen at room temperature. The mixture was then stirred for 18 hours before being quenched with ethyl acetate and water. The organic layer was removed and washed with sodium bicarbonate solution, dried (magnesium sulfate) and concentrated to give the sub-title product as an off-white solid (21.1 g, 96%); $^1$H NMR (400 MHz, CDCl$_3$) δ 1.43 (9H, s), 2.76 (1H, dd), 3.06 (1H, dd), 4.67-4.71 (1H, m), 5.12 (1h, d), 5.22 (1H, d), 5.86 (1H, d), 7.35-7.38 (5H, m); $^{19}$F NMR (376 MHz, CDCl$_3$) (proton decoupled) δ −139.98, −140.00, −140.04, −140.06, −157.05, −157.07, −157.11, −157.13; MS ES (+) 486.23 (M+H).

Method I:

(3S)-3-Benzyloxycarbonylamino-4-hydroxy-5-(2,3,5,6-tetrafluoro-phenoxy)-pentanoic acid tert-butyl ester

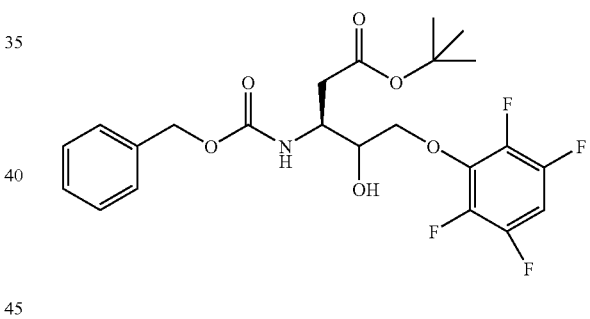

NaBH$_4$ (1.65 g) was added portionwise to a stirred solution of 3-benzyloxycarbonylamino-4-oxo-5-(2,3,5,6-tetrafluoro-phenoxy)-pentanoic acid tert-butyl ester (21.1 g) in anhydrous THF (220 mL) at −20° C. under nitrogen. After stirring at this temperature for 3 hours, the reaction was quenched by the addition of saturated ammonium chloride solution and diluted with DCM. The organic layer was removed and the aqueous layer re-extracted with DCM. The combined organic extracts were washed with brine, dried (magnesium sulfate) and concentrated. The residue was purified by column chromatography (10%-20% ethyl acetate/hexane). The sub-title compound as a white solid (14.6 g, 73%); $^1$H NMR (400 MHz, CDCl$_3$) δ 1.45 (9H, s), 2.61-2.77 (2H, m), 3.16-3.36 (1H, 2×brd d), 4.12-4.22 (2H, m), 4.30-4.33 (1H, m), 5.44-5.69 (1H, 2×d), 6.78-6.86 (1H, m), 7.35-7.36 (5H, m); $^{19}$F NMR (346 MHz, CDCl$_3$) (proton decoupled) δ −139.87, −139.89, −139.93, −139.95, −139.98, −157.02, −157.05,

−157.06, −157.08, −157.09, −157.10, −157.12; ES (+) 488.27 (M+H).

Method J:

(3S)-3-Amino-4-hydroxy-5-(2,3,5,6-tetrafluoro-phenoxy)-pentanoic acid tert-butyl ester

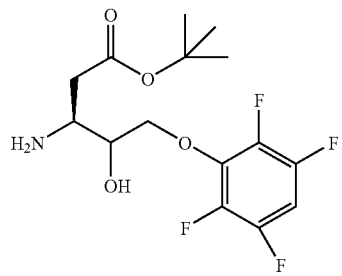

10% Pd on carbon (2.92 g) was added portionwise to a solution of 3-benzyloxycarbonylamino-4-hydroxy-5-(2,3,5,6-tetrafluoro-phenoxy)-pentanoic acid tert-butyl ester (14.6 g) in anhydrous MeOH (350 mL) which has been degassed under nitrogen (5×). The reaction was further degassed under nitrogen (3×) and hydrogen (5×) and stirred at room temperature for 20 minutes. The palladium residues were removed by filtration and the filtrate concentrated to give the sub-title compound as a white solid (9.5 g, 90%); $^1$H NMR (400 MHz, CDCl$_3$) δ 1.49 (9H, s), 2.35-2.43 (1H, m), 5.67-5.64 (1H, m), 3.37-3.43 (1H, m), 3.77-3.87 (1H, m), 4.28-4.63 (2H, m), 6.77-6.86 (1H, m); $^{19}$F NMR (346 MHz, CDCl$_3$) (proton decoupled) δ −139.95, −139.97, −140.00, −140.03, −140.05, −140.08, −140.11, −140.13, −157.15, −157.18, −157.21, −157.23, −157.27, −157.29.

S-3-[2-(7-chloro-1-oxo-1H-isoquinolin-2-yl)-butyrylamino]-4-oxo-5-(2,3,5,6-tetrafluoro-phenoxy)-pentanoic acid tert butyl ester

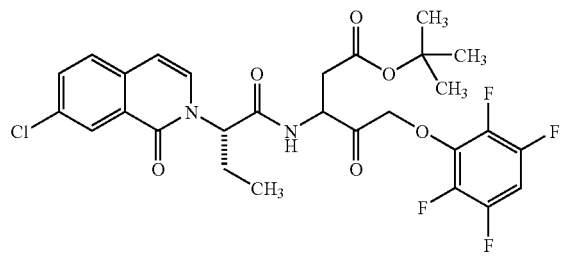

The titled compound was prepared using (S)-2-(7-Chloro-1-oxo-1H-isoquinolin-2-yl)-butyric acid (prepared as described in methods A-E) and (3S)-3-Amino-4-hydroxy-5-(2,3,5,6-tetrafluoro-phenoxy)-pentanoic acid tert-butyl ester (prepared as described in methods H-J) using procedures similar to those described in methods F-G. The product was isolated as a white solid.

$^1$H NMR (400 MHz, CDCl$_3$) δ 0.99 (3H, t), 1.33 (9H, s), 1.98-2.03 (1H, m), 2.26-2.33 (1H, m), 2.70 (1H, dd), 2.91 (1H, dd), 4.83-4.88 (1H, m), 5.05 (1H, d), 5.15 (1H, d), 5.47 (1H, t), 6.57 (1H, d), 6.76-6.81 (1H, m), 7.25 (1H, d), 7.31 (1H, d), 7.49 (1H, d), 7.61 (1H, dd), 8.36 (1H, s); $^{19}$F NMR (376 MHz, CDCl$_3$)(proton decoupled) δ −139.86, 31 139.88, −139.92, −139.94, −157.09, −157.12, −157.15 and −157.17; ES(−) 597.3.

EXAMPLE 7

S-3-[2-(7-trifluoromethyl-1-oxo-1H-isoquinolin-2-yl)-butyrylamino]-4-oxo-5-(2,3,5,6-tetrafluoro-phenoxy)-pentanoic acid

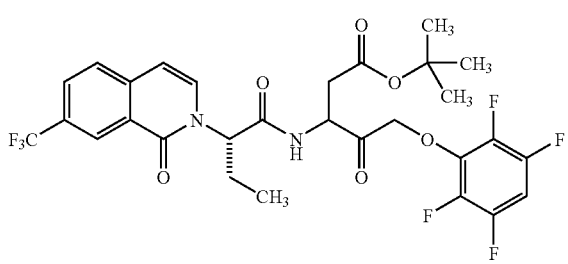

This compound was prepared using methods similar to A-G and was isolated as a white solid $^1$H NMR (400 MHz, CDCl$_3$) δ 1.00 (3H, t), 1.40 (9H, s), 2.00-2.50 (2H, 2m), 2.70-3.05 (2H, 2m), 4.95 (1H, m, CH), 5.10 (2H, dd), 5.55 (1H, t), 6.65 (1H, d), 6.80 (1H, m), 7.35 (1H, d), 7.65 (1H, d), 7.85 (1H, d), 8.70 (1H, s); $^{19}$F NMR (376 MHz, CDCl$_3$)(proton decoupled) δ −62.88, −139.85, −157.13; ES(+) 633.3, ES(−) 631.3

EXAMPLE 8

S-3-[2-(7-chloro-1-oxo-1H-isoquinolin-2-yl)-butyrylamino]-5-fluoro-4-oxo-pentanoic acid ethyl ester

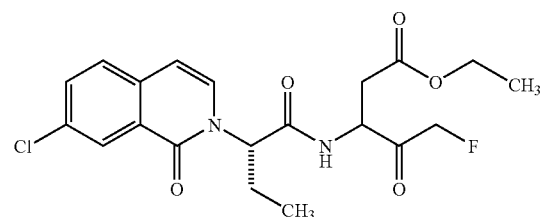

Method K:

S-3-[2-(7-chloro-1-oxo-1H-isoquinolin-2-yl)-butyrylamino]-5-fluoro-4-oxo-pentanoic acid

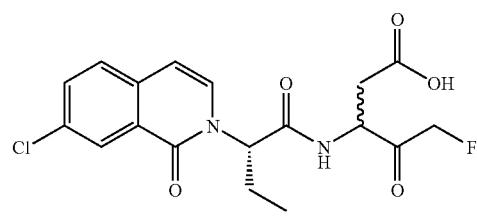

A solution of S-3-[2-(7-chloro-1-oxo-1H-isoquinolin-2-yl)-butyrylamino]-5-fluoro-4-oxo-pentanoic acid tert butyl ester (10 g) in dichloromethane (500 mL) was cooled to 0° C. Trifluoroacetic acid (120 mL) was added portionwise and the resulting mixture was stirred at 0° C. for one hour and then allowed to warm to ambient temperature during two hours. The mixture was then concentrated under reduced pressure and the residue redissolved in dichloromethane. This process was repeated several times in order to remove excess trifluoroacetic acid. The solid was then dried to constant weight under vacuum. The product was isolated as a white solid (8.5 g, 97%); IR (solid) 1782.7, 1741.7, 1644.4, 1593.2, 1536.8, 1209.1, 1168.1, 1055.5, 840.4 cm-$^1$; $^1$H NMR (400 MHz, d6-DMSO) δ 0.82 (3H, m), 1.81-2.25 (2H, m), 2.25-3.11 (2H, m), 4.15-5.60 (4H, m), 6.70 (1H, m), 7.55 (1H, m), 7.78 (2H, m), 8.15 (1H, s), 8.35-9.00 (1H, brm); $^{13}$C NMR (100 MHz, d6-DMSO) δ 10.6, 23.0, 24.0, 24.6, 32.9, 34.6, 34.7, 47.7, 52.2, 52.3, 58.2, 58.23, 58.7, 59.1, 83.4, 83.5, 85.2, 85.3, 103.9, 104.5, 104.7, 104.8, 126.5, 126.6, 128.8, 131.3, 131.4, 131., 133.1, 135.7, 135.73, 160.8, 170.2, 170.3, 170.4, 172.0, 173.1, 202.6, 202.7; $^{19}$F NMR (376 MHz, d6-DMSO) δ −226.70, −226.75, −227.51, −230.5, −231.16, −232.61, −232.67, −233.37; ES(+) 397.2, ES(−) 395.3.

Method L:

S-3-[2-(7-chloro-1-oxo-1H-isoquinolin-2-yl)-butyrylamino]-5-fluoro-4-oxo-pentanoic acid ethyl ester A solution of S-3-[2-(7-chloro-1-oxo-1H-isoquinolin-2-yl)-butyrylamino]-5-fluoro-4-oxo-pentanoic acid (100 mg) in dichloromethane (1 mL) was cooled to 0° C. under nitrogen. N,N'-Carbonyldiimidazole (42 mg) was added in one portion and the reaction was stirred at 0° C. for 20 minutes, then allowed to warm to ambient temperature during 30 minutes. Ethanol (60 mg) in dichloromethane (0.2 mL) was added and the reaction stirred at ambient temperature for 18 hours then concentrated in vacuo. The residue was purified by column chromatography (30% ethyl acetate/hexane to 50% ethyl acetate/hexane) to afford the title compound as a viscous oil (65 mg, 61%); $^1$H NMR (400 MHz, CDCl$_3$) δ 0.85-1.01 (3H, m), 1.05-1.30 (3H, m), 1.95 (1H, m), 2.25 (1H, m), 2.72-3.09 (2H, m), 3.90-4.18 (2H, m), 4.80-5.30 (3H, m), 5.56 (1H, m), 6.60 (1H, m), 7.15-7.85 (4H, m), 8.21 (1H, m); $^{19}$F (376 MHz, CDCl$_3$) δ −231.74, −232.08; ES(+) 425.2, ES(−) 423.3.

EXAMPLE 9

S-3-[2-(7-chloro-1-oxo-1H-isoquinolin-2-yl)-butyrylamino]-5-fluoro-4-oxo-pentanoic acid propyl ester

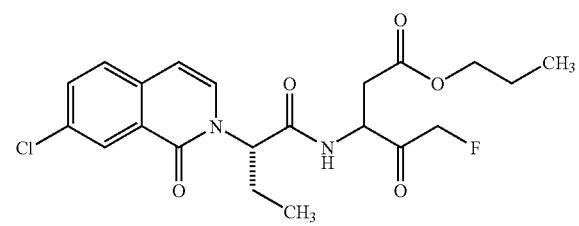

This was prepared using procedure similar to that described in Method L. The product was isolated as a viscous oil (51%); $^1$H NMR (400 MHz, CDCl$_3$) δ 0.75-1.05 (6H, m), 1.35-1.65 (2H, m), 1.95 (1H, m), 2.25 (1H, m), 2.75-3.09 (2H, m), 3.80-4.05 (2H, m), 4.89-5.30 (3H, m), 5.52 (1H, m), 6.60 (1H, m), 7.15-7.80 (4H, m), 8.25 (1H, m); $^{19}$F NMR (376 MHz, CDCl$_3$) δ −231.74, −232.08; ES(+) 439.3, ES(−) 437.3.

EXAMPLE 10

S-3-[2-(7-chloro-1-oxo-1H-isoquinolin-2-yl)-butyrylamino]-5-fluoro-4-oxo-pentanoic acid 3,3,3-trifluoro-propyl ester

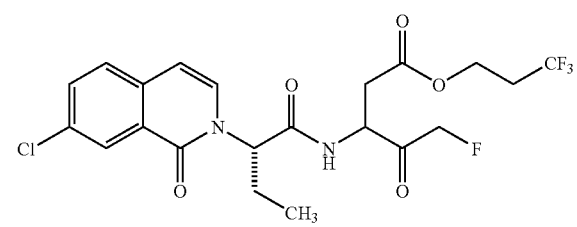

This was prepared using procedure similar to that described in Method L. The product was isolated as a viscous oil (32%); $^1$H NMR (400 MHz, CDCl$_3$) δ 1.00 (3H, m), 1.98 (1H, m), 2.13-2.52 (3H, m), 2.80-3.09 (2H, m), 4.09-4.30 (2H, m), 4.75-5.21 (3H, m), 5.50 (1H, m), 6.61 (1H, m), 7.15-7.82 (4H, m), 8.26 (1H, m); $^{19}$F NMR (376 MHz, CDCl$_3$) δ −231.76, −231.80, −65.49, −65.54; ES(+) 493.2, ES(−) 491.2.

EXAMPLE 11

S-3-[2-(7-chloro-1-oxo-1H-isoquinolin-2-yl)-butyrylamino]-5-fluoro-4-oxo-pentanoic acid isopropyl ester

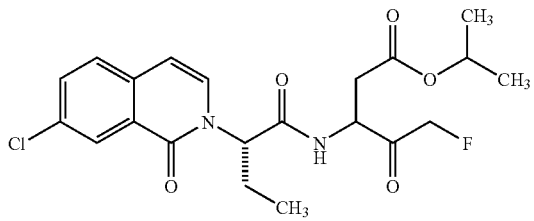

This was prepared using procedure similar to that described in Method L. The product was isolated as a viscous oil (27%); $^1$H NMR (400 MHz, CDCl$_3$) δ 1.02 (3H, m), 1.05-1.35 (6H, m), 1.98 (1H, m), 2.25 (1H, m), 2.72-3.05 (2H, m), 4.75-5.30 (4H, m), 5.50 (1H, m), 6.60 (1H, m), 7.15-7.70 (4H, m), 8.25 (1H, m); $^{19}$F (376 MHz, CDCl$_3$) δ −231.76, −232.12; ES(+) 439.2, ES(−) 437.3.

EXAMPLE 12

S-3-[2-(7-chloro-1-oxo-1H-isoquinolin-2-yl)-butyrylamino]-5-fluoro-4-oxo-pentanoic acid benzyl ester

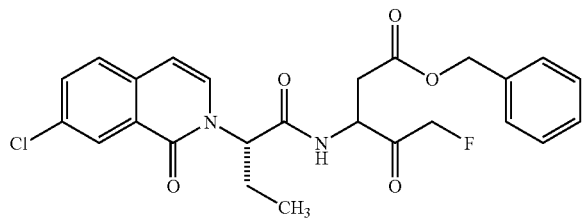

This was prepared using procedure similar to that described in Method L. The product was isolated as a viscous oil (53%); $^1$H NMR (400 MHz, CDCl$_3$) δ 0.82-1.00 (3H, m), 1.95 (1H, m), 2.23 (1H, m), 2.82-3.09 (2H, m), 4.80-5.28 (5H, m), 5.55 (1H, m), 6.60 (1H, m), 7.15-7.60 (8H, m), 7.68-7.85 (1H, m), 8.20 (1H, m); $^{19}$F NMR (376 MHz, CDCl$_3$) δ −231.62, −231.89; ES(+) 487.2, ES(−) 485.3.

EXAMPLE 13

(S,S)-3-[2-(1-oxo-1H-isoquinolin-2-yl)-butyrylamino]-4-oxo-5-(2,3,5,6-tetrafluoro-phenoxy)-pentanoic acid tert butyl ester

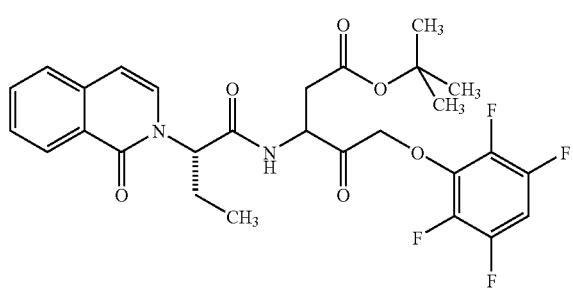

This compound was prepared using (S)-2-(1-oxo-1H-isoquinolin-2-yl)-butyric acid (prepared from 2-formylbenzoic acid using procedures similar to those described in methods A-E) and (3S)-3-Amino-4-hydroxy-5-(2,3,5,6-tetrafluoro-phenoxy)-pentanoic acid tert-butyl ester (prepared as described in methods H-J) using procedures similar to those described in methods F-G. This compound was isolated as a white solid This compound was prepared using methods similar to A-G and was isolated as a white solid $^1$H NMR (400 MHz, CDCl$_3$) δ 0.98 (3H, t), 1.30 (9H, s), 1.98-2.02 (1H, m), 2.26-2.32 (1H, m), 2.68 (1H, dd), 2.90 (1H, dd), 4.83-4.88 (1H, m), 5.06 (1H, d), 5.15 (1H, d), 5.50 (1H, t), 6.60 (1H, d), 6.75-6.82 (1H, m), 7.23 (1H, d), 7.33 (1H, d), 7.49-7.55 (1H, m), 7.68 (1H, t), 8.41 (1H, d); $^{19}$F NMR (376 MHz, CDCl$_3$)(proton decoupled) δ −139.94, −139.97, −140.0, −140.02. −157/06, −157.09, −157.12, −157.14; ES(+) 565.3, ES(−) 563.3.

EXAMPLE 14

S-3-[2-(7-chloro-1-oxo-1H-isoquinolin-2-yl)-butyrylamino]-4-oxo-5-(2,3,5,6-tetrafluoro-phenoxy)-pentanoic acid methyl ester

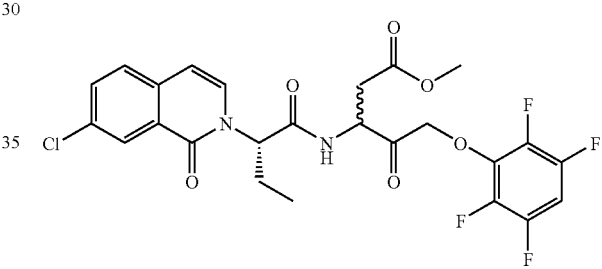

Method M:

S-3-[2-(7-chloro-1-oxo-1H-isoquinolin-2-yl)-butyrylamino]-4-oxo-5-(2,3,5,6-tetrafluoro-phenoxy)-pentanoic acid

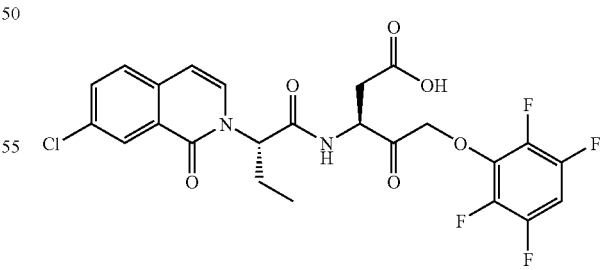

A solution of S-3-[2-(7-chloro-1-oxo-1H-isoquinolin-2-yl)-butyrylamino]-4-oxo-5-(2,3,5,6-tetrafluoro-phenoxy)-pentanoic acid tert butyl ester (7.4 g) in dichloromethane (100 mL) was cooled to 0° C. 50% Trifluoroacetic acid in dichloromethane (100 mL) was added and the resulting mixture stirred at 0° C. for one hour and then allowed to warm to ambient temperature during two hours. The mixture was then concentrated under reduced pressure and the residue redissolved in dichloromethane. This process was repeated several times in order to remove excess trifluoroacetic acid. The solid was then dried to constant weight under vacuum. The product was isolated as a white solid (6.1 g, 94%); IR (solid) 1639.3, 1618.8, 1593.2, 1516.4, 1485.6, 1219.4, 1168.1, 1106.7, 932.6, 830.2 cm$^{-1}$; $^1$H NMR (400 MHz, d6-DMSO) δ 0.80 (3H, t), 1.94-2.12 (2H, m), 2.55-2.61 (1H, m), 2.74-2.80 (1H, m), 4.58-4.63 (1H, m), 5.12-5.76 (3H, m), 6.70 (1H, d), 7.51-7.78 (4H, m), 8.11-8.12 (1H, m), 8.60-8.95 (1H, 3d); $^{13}$C NMR (100 MHz, d6-DMSO) δ 23.85, 24.52, 32.99, 34.67, 47.87, 52.81, 55.26, 58.25, 58.91, 74.43, 75.65, 100.10, 100.34, 100.58, 101.05, 101.29, 104.65, 126.51, 136.61, 131.31, 131.40, 133.04, 135.64, 135.68, 139.03, 139.18, 141.47, 141.62, 144.68, 144.80, 144.90, 147.10, 147.19, 160.78, 170.45, 172.07, 173.02, 202.2; $^{19}$F NMR (376 MHz, d6-DMSO) δ −140.57, −140.60, −140.64, −140.66, −141.00, −141.03, −141.06, −141.09, −156.78, −156.80, −156.84, −156.86, −156.96, −156.98, −157.02, −157.04; ES(+) 543.2, ES(−) 541.3.

Method N:

S-3-[2-(7-chloro-1-oxo-1H-isoquinolin-2-yl)-butyrylamino]-4-oxo-5-(2,3,5,6-tetrafluoro-phenoxy)-pentanoic acid methyl ester

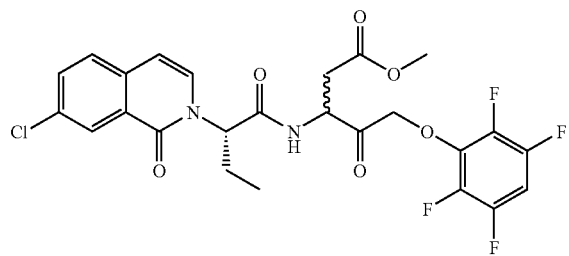

A solution of S-3-[2-(7-chloro-1-oxo-1H-isoquinolin-2-yl)-butyrylamino]-4-oxo-5-(2,3,5,6-tetrafluoro-phenoxy)-pentanoic acid (100 mg) in dichloromethane (1 mL) was cooled to 0° C. under nitrogen. N,N'-Carbonyldiimidazole (35 mg) was added in one portion and the reaction was stirred at 0° C. for 20 minutes, then allowed to warm to ambient temperature during 30 minutes. Methanol (29 mg) in dichloromethane (0.2 mL) was added and the reaction stirred at room temperature for 18 hours then concentrated in vacuo. The residue was purified by column chromatography (20% ethyl acetate/hexane) to afford the title compound as a white solid (42 mg, 41%); IR (solid) 3294.6, 3075.4, 2946.7, 1731.6, 1641.1, 1622.0, 1588.7, 1512.4, 1483.8, 1436.2, 1369.5, 1331.3, 1274.2, 1217.0, 1169.3, 1102.6, 940.6, 902.5, 831.0, 783.4, 707.1, 688.1; $^1$H NMR (400 MHz, CDCl$_3$) δ 0.96-1.00 (3H, m), 1.99-2.08 (1H, m), 2.25-2.32 (1H, m), 2.81-2.87 (1H, m), 2.97-3.15 (1H, 2dd), 3.57 & 3.70 (3H, 2s), 4.74-5.10 (3H, m), 5.43-5.49 (1H, 2t), 6.58 (1H, 2d), 6.71-82 (1H, m), 7.25 (1H, 2d), 7.30-7.51 (2H, m), 7.62 (1H, 2d), 8.37 (1H, 2d); $^{19}$F NMR (376 MHz, CDCl$_3$) δ −139.73, −139.75, −139.76, −139.79, −139.80, −139.81, −139.82, −157.12, −157.14, −157.18, −157.20, −157.23, −157.26, −157.29; ES(+) 557.2, ES(−) 555.3.

EXAMPLE 15

S-3-[2-(7-chloro-1-oxo-1H-isoquinolin-2-yl)-butyrylamino]-4-oxo-5-(2,3,5,6-tetrafluoro-phenoxy)-pentanoic acid ethyl ester

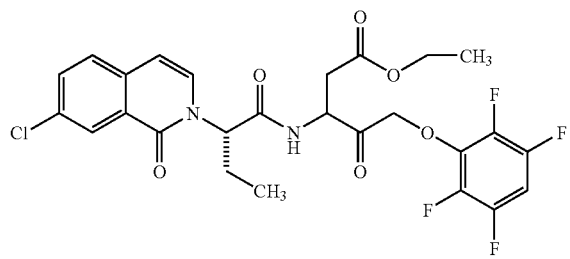

This was prepared from S-3-[2-(7-chloro-1-oxo-1H-isoquinolin-2-yl)-butyrylamino]-4-oxo-5-(2,3,5,6-tetrafluoro-phenoxy)-pentanoic acid using procedure similar to that described in Method N. The product was isolated as a white solid (41%); IR (solid) 3289.8, 3056.3, 2937.2, 1731.6, 1645.9, 1612.5, 1588.7, 1517.2, 1483.8, 1431.4, 1369.5, 1269.4, 1174.1, 1102.6, 1031.1, 940.6, 893.0, 831.0, 711.9, 683.3; $^1$H NMR (400 MHz, CDCl$_3$) δ 0.96-1.01 (3H, m), 1.71 & 1.26 (3H, 2t), 1.92-2.08 (1H, m), 2.21-2.32 (1H, m), 2.79-2.83 (1H, m), 2.94-3.12 (1H, 2dd), 4.02 & 4.15 (2H, 2q), 4.72-5.06 (3H, m), 5.41-5.48 (1H, 2t), 6.58 (1H, 2d), 6.69-6.83 (1H, m), 7.24-7.31 (1.5 H, m), 7.46-7.51 (1.5H, m), 7.62 (1H, 2d), 8.37 (1H, 2d); $^{19}$F NMR (376 MHz, CDCl$_3$) δ −139.75, −139.77, −139.80, −139.80, −139.83, −139.86, −157.08, −157.10, −157.14, −157.16, −157.18, −157.21, −157.24, −157.26; ES(+) 571.2, ES(−) 569.4.

EXAMPLE 16

S-3-[2-(7-chloro-1-oxo-1H-isoquinolin-2-yl)-butyrylamino]-4-oxo-5-(2,3,5,6-tetrafluoro-phenoxy)-pentanoic acid propyl ester

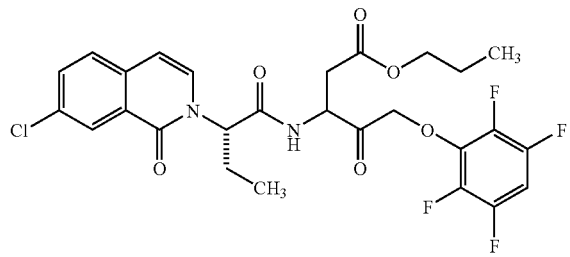

This was prepared from S-3-[2-(7-chloro-1-oxo-1H-isoquinolin-2-yl)-butyrylamino]-4-oxo-5-(2,3,5,6-tetrafluoro-phenoxy)-pentanoic acid using procedure similar to that described in Method N. The product was isolated as a white solid (74%); IR (solid) 3298.4, 2965.6, 2940.0, 2868.3, 1731.4, 1654.6, 1623.9, 1598.3, 1511.2, 1485.6, 1270.6, 1168.1, 1101.6, 937.7, 819.9, 717.5; $^1$H NMR (400 MHz, CDCl$_3$) δ 0.84-1.00 (6H, m), 1.53-1.65 (2H, 2q), 1.95-2.03 (1H, m), 2.26-2.32 (1H, m), 2.79-2.84 (1H, m), 2.96-3.14

(1H, 2dd), 3.91 & 4.05 (2H, 2t), 4.75-5.12 (3H, m), 5.41-5.46 (1H, 2t), 6.58 (1H, 2d), 6.70-6.82 (1H, m), 7.25 (1H, 2d), 7.30-7.50 (2H, m), 7.62 (1H, 2d), 8.36 (1H, 2d); $^{19}$F NMR (376 MHz, CDCl$_3$) δ −139.76, −139.78, −139.80, −139.82, −139.84, −139.86, −157.06, −157.08, −157.12, −157.14, −157.17, −157.19, −157.23, −157.25; ES(+) 585.2, ES(−) 583.3.

EXAMPLE 17

S-3-[2-(7-chloro-1-oxo-1H-isoquinolin-2-yl)-butyrylamino]-4-oxo-5-(2,3,5,6-tetrafluoro-phenoxy)-pentanoic acid 3,3,3-trifluoro-propyl ester

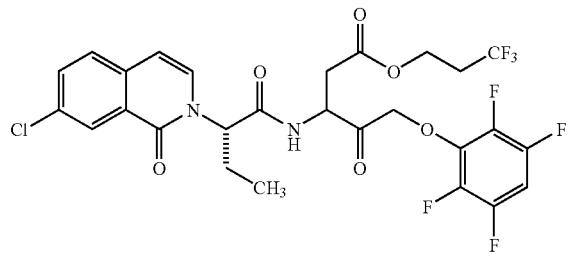

This was prepared from S-3-[2-(7-chloro-1-oxo-1H-isoquinolin-2-yl)-butyrylamino]-4-oxo-5-(2,3,5,6-tetrafluorophenoxy)-pentanoic acid using procedure similar to that described in Method N. The product was isolated as a white solid (39%); IR (solid) 3303.6, 2965.6, 2929.7, 1746.8, 1644.4, 1618.8, 1593.2, 1516.4, 1490.8, 1367.9, 1255.2, 1157.9, 1137.4, 1106.7, 1009.4, 942.8, 835.3, 712.4; $^1$H NMR (400 MHz, CDCl$_3$) δ 0.96-1.01 (3H, m), 1.93-2.01 (1H, m), 2.19-2.62 (3H, m), 2.84-2.90 (1H, m), 2.95-3.14 (1H, 2dd), 4.20 & 4.32 (2H, 2t), 4.72-5.09 (3H, m), 5.40-5.45 (1H, 2t), 6.58 (1H, 2d), 6.70-6.81 (1H, m), 7.25 (1H, 2d), 7.34-7.51 (2H, m), 7.62 (1H, 2d), 8.36 (1H, 2d); $^{19}$F (376 MHz, CDCl$_3$) δ −64.49, −65.53, −139.67 −139.69, −139.73, −139.75, −157.17, −157.20, −157.23, −157.25, −157.28, −157.31, −157.33; ES(+) 639.4, ES(−) 637.6.

EXAMPLE 18

S-3-[2-(7-chloro-1-oxo-1H-isoquinolin-2-yl)-butyrylamino]-4-oxo-5-(2,3,5,6-tetrafluoro-phenoxy)-pentanoic acid isopropyl ester

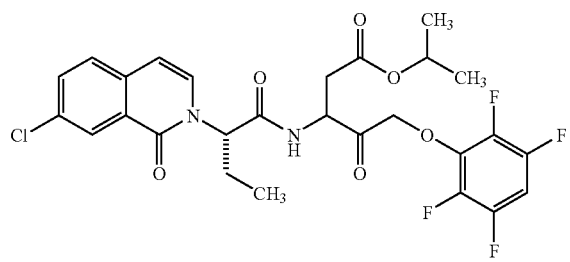

This was prepared from S-3-[2-(7-chloro-1-oxo-1H-isoquinolin-2-yl)-butyrylamino]-4-oxo-5-(2,3,5,6-tetrafluorophenoxy)-pentanoic acid using procedure similar to that described in Method N. The product was isolated as a white solid (33%); IR (solid) 3283.1, 2980.9, 2929.7, 2878.5, 1731.4, 1654.6, 1618.8, 1598.3, 1511.2, 1485.6, 1373.0, 1332.0, 1275.7, 1214.2, 1173.3, 1111.8, 978.7, 937.7, 901.9, 825.0, 712.4; $^1$H NMR (400 MHz, CDCl$_3$) δ 0.96-1.00 (3H, m), 1.13-1.17 (3H, m), 1.24 (3H, d), 1.98-2.06 (1H, m), 2.24-2.31 (1H, m), 2.73-2.78 (1H, m), 2.81-3.12 (1H, 2dd), 4.73-5.12 (4H, m), 5.41-5.47 (1H, dt), 6.58 (1H, 2d), 6.72-6.84 (1H, m), 7.25 (1H, 2d), 7.31-7.50 (2H, m), 7.62 (1H, 2d), 8.37 (1H, 2d); $^{19}$F NMR (376 MHz, CDCl$_3$) δ −139.75, −139.78, −139.80, −139.81, −139.82, −139.84, −139.86, −139.88, −157.04, −157.06, −157.10, −157.12, −157.16, −157.18, −157.21, −157.24; ES(+) 585.2, ES(−) 583.3.

EXAMPLE 19

S-3-[2-(7-chloro-1-oxo-1H-isoquinolin-2-yl)-butyrylamino]-4-oxo-5-(2,3,5,6-tetrafluoro-phenoxy)-pentanoic acid benzyl ester

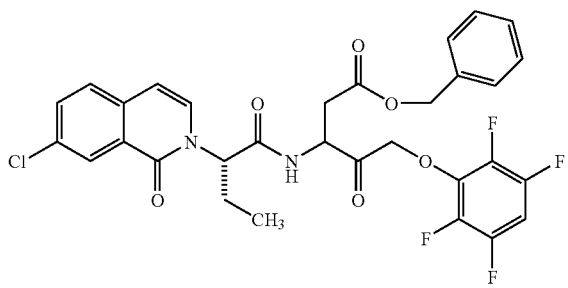

This was prepared from S-3-[2-(7-chloro-1-oxo-1H-isoquinolin-2-yl)-butyrylamino]-4-oxo-5-(2,3,5,6-tetrafluorophenoxy)-pentanoic acid using procedure similar to that described in Method N. The product was isolated as a white solid (36%); IR (solid) 3285.1, 3061.1, 2951.5, 1736.4, 1650.6, 1626.8, 1593.4, 1512.4, 1488.6, 1388.3, 1280.8, 1174.1, 1102.6, 937.7, 835.3, 748.2; $^1$H NMR (400 MHz, CDCl$_3$) δ 0.93-1.00 (3H, m), 1.93-2.02 (1H, m), 2.24-2.28 (1H, m), 2.86-2.92 (1H, m), 2.99-3.19 (1H, 2dd), 4.74-5.14 (5H, m), 5.40-5.44 (1H, 2t), 6.57 (1H, 2d), 6.70-6.84 (1H, m), 7.23 (1H, d), 7.34-7.49 (7H, m), 7.61-7.63 (1H, m), 8.38 (1H, 2d); $^{19}$F (376 MHz, CDCl$_3$) δ −139.72, −139.74, −139.78, −139.81, −139.83, −157.06, −157.08, −157.12, −157.14, −157.18, −157.20, −157.23, −157.26; ES(+) 633.4, ES(−) 631.6.

EXAMPLE 20

S-3-[2-(6-chloro-1-oxo-1H-isoquinolin-2-yl)-butyrylamino]-5-fluoro-4-oxo-pentanoic acid tert-butyl ester

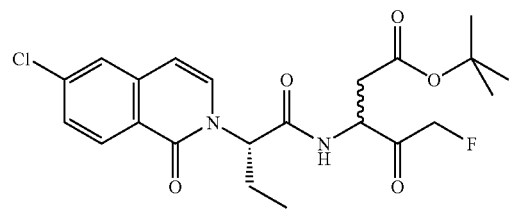

Method O:

4-Chloro-N-methyl-benzamide

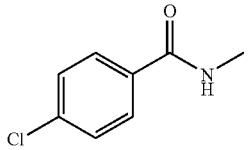

To a 0° C. solution of the 4-chlorobenzoyl chloride (4.50 g) in dichloromethane (10 mL) was added an 8M solution of methylamine in ethanol dropwise. The solution was stirred for 16 h and then evaporated to dryness. The residue was diluted with saturated sodium bicarbonate solution (10 mL) and extracted three times with ethyl acetate (3×20 mL), the organics washed with brine (10 mL), dried (MgSO$_4$) and concentrated in vacuo to afford the sub-title compound as a white solid (4.33 g; 97%): $^1$H NMR (400 MHz, CDCl3) δ 3.00 (3H, s), 7.40 (1H, brs) 7.40 (1H, d), 7.70 (1H, d).

Method P:

2-formyl-4-chloro-N-methylbenzamide

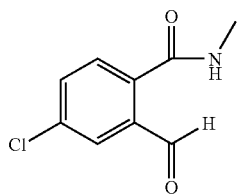

To a solution of 4-chloro-N-methyl-benzamide (3.1 g) in THF (30 mL) was added n-butyl lithium (30.1 mL of 2.5M hexane solution) and the solution refluxed for 45 min. The solution was then cooled to 0° C. and N-methylformanilide (9.27 mL) added dropwise over 2 min. The solution was then refluxed for 2 h and then cooled to ambient temperature, water (80 mL) added and the solution acidified to pH 1 with 2M HCl. The solution was then extracted three times with ethyl acetate (3×50 mL), washed with brine (20 mL), dried (MgSO$_4$) and concentrated in vacuo. The resulting brown oil was purified on silica by flash chromatography to afford the sub-titled product as a pale yellow solid (2.13 g; 59%); $^1$H NMR (400 MHz, CDCl3) δ 2.90 (3H, s), 4.25 (1H, d) 5.60 (1H, d), 7.35 (2H, s), 7.60 (1H, s).

Method Q

2-Formyl-4-chlorobenzoic acid

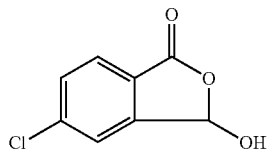

A mixture of 2-formyl-4-chloro-N-methylbenzamide (3.19 g) and 10M hydrochloric acid (30 ml) was heated at reflux for 18 hours. The mixture was cooled and basified with saturated sodium hydrogen carbonate solution. The solution was then washed with ethyl acetate, then acidified with 2M hydrochloric acid. The product was extracted with ethyl acetate and the combined extracts dried with magnesium sulfate. The solution was then filtered and concentrated. This furnished 2-formyl-4-chlorobenzoic acid as a yellow solid (2.22 g, 75%); $^1$H NMR (400 MHz, CDCl3) δ 6.65 (0.5H, brs), 7.50 (2H, m), 7.65 (1H, m), 7.85 (0.5H, brm), 8.05 (1H, m).

S-3-[2-(6-chloro-1-oxo-1H-isoquinolin-2-yl)-butyrylamino]-5-fluoro-4-oxo-pentanoic acid tert-butyl ester

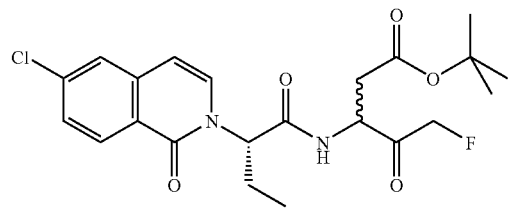

This was prepared from 2-formyl-4-chlorobenzoic acid (prepared as described in methods O-Q) using procedures similar to those described in methods A-G.

The title compound was isolated by preparative HPLC and was obtained as a white solid; $^1$H NMR (400 MHz, CDCl$_3$) δ 0.97 (3H, m), 1.90-2.31 (2H, m), 2.65-3.30 (2H, m), 4.20-5.75 (4H, m), 6.65 (1H, m), 7.40-7.60 (3H, m), 8.29 (1H, m), 9.20 (1H, br); $^{19}$F NMR (376 MHz, CDCl$_3$) (proton decoupled) δ −229.80, −232.07, −232.43, −232.58, −232.78; MS ES (−) 395.26 (M−H).

EXAMPLE 21

5-3-[2-(6-trifluoromethyl-1-oxo-1H-isoquinolin-2-yl)-butyrylamino]-5-fluoro-4-oxo-pentanoic acid tert-butyl ester

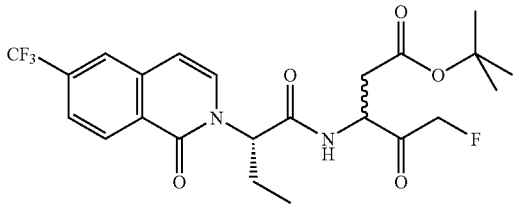

The above compound was prepared from 2-Formyl-4-trifluoromethylbenzoic acid (prepared from 4-trifluoromethylbenzoic acid using methods similar to those described in O-Q) using procedures similar to those described in methods A-G. The title compound was isolated as a white solid (95%, last step); $^1$H NMR (400 MHz, CDCl$_3$) δ 0.99 (3H, m), 1.90-2.30 (2H, m), 2.60-3.50 (2H, m), 4.20-5.75 (4H, m), 6.80 (1H, m), 7.50-7.90 (3H, m), 7.92 (1H, m), 8.40-8.60 (1H, m); $^{19}$F NMR (376 MHz, d6-DMSO) (proton decoupled) δ

−63.60, −63.61, −63.65, −231.67, −231.80, −232.06, −232.18; MS ES(+) 431.26 (M+H).

EXAMPLE 22

(S,S)-3-[2-(6,7-dichloro-1-oxo-1H-isoquinolin-2-yl)-butyrylamino]-4-oxo-5-(2,3,5,6-tetrafluoro-phenoxy)-pentanoic acid tert-butyl ester

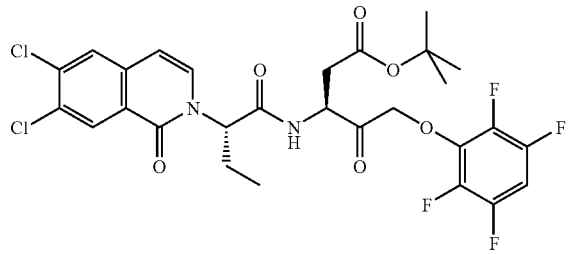

Method R:

5,6-Dichloro-3H-isobenzofuran-1-one

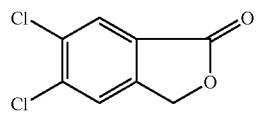

NaBH$_4$ (5.2 g) was added to a stirred solution of 4,5-dichlorophthalic anhydride (20 g) in anhydrous DMF (100 mL) at 0° C. under nitrogen in small portions over 1 hour. The reaction was warmed to room temperature for a further 2 hours and poured into ice/1M HCl. The resultant white precipitate (4,5-dichloro-2-hydroxymethyl-benzoic acid) was collected by filtration and dried under vacuum. The precipitate was suspended in toluene (200 mL) with catalytic pTSA and heated to reflux under Dean-Stark conditions (precipitate dissolves on heating) for 18 hours. The reaction was cooled to room temperature and the resultant white precipitate collected by filtration to give the sub-title compound as a white solid (14.0 g, 75%); $^1$H NMR (400 MHz, d6-DMSO) δ 5.40 (2H, s), 8.05 (1H, s), 8.15 (1H, s).

Method S:

3-Bromo-5,6-Dichloro-3H-isobenzofuran-1-one

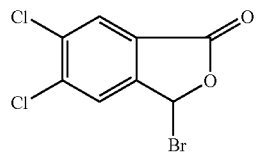

A suspension of 5,6-Dichloro-3H-isobenzofuran-1-one (1.45 g), N-bromosuccinimide (1.27 g) and catalytic benzoyl peroxide in chloroform (30 mL) was heated to reflux for 1 hour. After cooling, the reaction mixture was washed with water, brine, dried (magnesium sulfate), filtered and concentrated to give the sub-title compound as a white solid (1.82 g, 91%); $^1$H NMR (400 MHz, CDCl$_3$) δ 7.36 (1H, s), 7.77 (1H, s), 8.03 (1H, s).

Method T:

4,5-Dichloro-2-formyl-benzoic acid

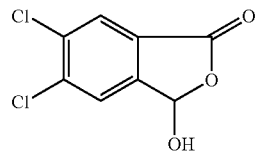

A suspension of 3-bromo-5,6-dichloro-3H-isobenzofuran-1-one (2.0 g) in 5% aqueous HCl (10 mL) and 80% aqueous dioxane (25 mL) were heated to reflux for 2 hours. The solvent was removed and the resulting residue re-dissolved in ethyl acetate, dried (magnesium sulfate) and concentrated. The resultant yellow solid was recrystallized from DCM/hexane to give the sub-title compound as a white solid (1.13 g, 73%); $^1$H NMR (400 MHz, CDCl$_3$) δ 6.66 (0.84H, s), 7.95 (0.16H, s), 8.05 (0.84H), 8.12 (0.16H, s), 8.14 (0.84H, s), 8.41 (0.84H,), 10.41 (0.16H, s), 11.07 (0.16 H, brs).

(S,S)-3-[2-(6,7-dichloro-1-oxo-1H-isoquinolin-2-yl)-butyrylamino]-4-oxo-5-(2,3,5,6-tetrafluoro-phenoxy)-pentanoic acid tert-butyl ester

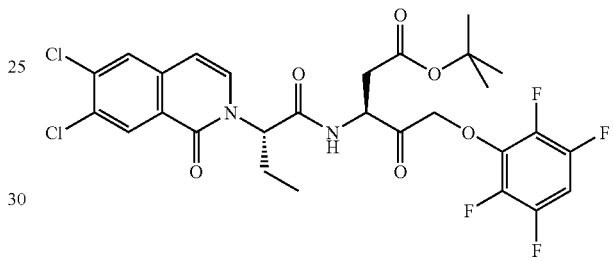

This compound was prepared using (S)-2-(6,7-dichloro-1-oxo-1H-isoquinolin-2-yl)-butyric acid (synthesized from 4,5-dichloro-2-formyl-benzoic acid [prepared as described in methods R-T] using procedures similar to those described in methods A-E) and (3S)-3-Amino-4-hydroxy-5-(2,3,5,6-tetrafluoro-phenoxy)-pentanoic acid tert-butyl ester (prepared as described in methods H-J) using procedures similar to those described in methods F-G. The title compound was isolated as a white solid (94% last step); IR (solid) 1784.5, 1734.7, 1650.1, 1610.2, 1585.4, 1515.7, 1490.8, 1426.0, 1216.9, 1172.1, 1092.5, 933.1 cm$^{-1}$; $^1$H NMR (400 MHz, d6-DMSO) δ 0.80 (3H, t), 1.90-1.98 (1H, m), 2.04-2.12 (1H, m), 2.55-2.79 (2H, m), 4.56-4.71 (1H, m), 5.08-5.41 (3H, m), 6.67 (1H, d), 7.56-7.59 (2H, m), 8.07 (1H, brs), 8.25 (1H, d), 8.85-8.95 (1H, 2×d), 12.73 (1H, brs); $^{19}$F NMR (376 MHz, d6-DMSO) (proton decoupled) δ −140.93, −140.95, −140.99, −141.01, −141.04, −141.07, −141.10, −156.76, −156.79, −156.82, −156.85, −156.89, −156.91; MS ES (+): 577.14 (M+H).

EXAMPLE 23

S-3-[2-(7-chloro-1-oxo-1H-isoquinolin-2-yl)-butyrylamino]-4-oxo-5-(2,3,5,6-tetrafluoro-phenoxy)-pentanoic acid cyclohexyl ester

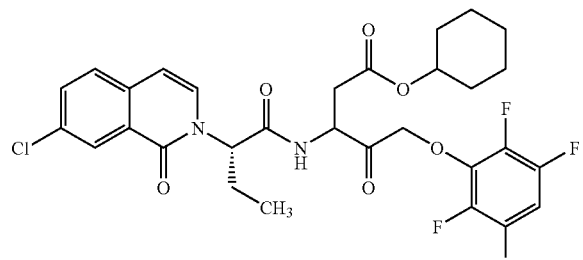

This was prepared using procedures similar to that described in Method N. The product was isolated as a white solid (24%); IR (solid) 1639,1586, 1518, 1485, 832; $^1$H NMR (400 MHz, CDCl$_3$) δ 0.96-1.00 (3H, m), 1.22-1.37 (6H, m), 1.51-1.55 (1H, m), 1.66-1.72 (3H, m), 1.90-1.95 (1H, m), 2.00 (1H, dd), 2.26-2.34 (1H, m), 2.79 (1H, 2dd), 3.03 (1H, 2dd), 4.73-5.11 (2H, 2dd), 4.89-4.94 (1H, m), 5.45 (1H, dd), 6.57-6.60 (1H, m), 6.71-6.81 (1H, m), 7.24 (1H, d), 7.42-7.50 (2H, m), 7.62 (1H, dd), 8.39 (1H, dd); $^{19}$F (376 MHz, CDCl$_3$) δ −139.74, −139.76, −139.79, −139.80, −139.82, −139.84, −156.96, −156.98, −157.01, −157.04, −157.09, −157.11, −157.15, −157.17; ES(+) 625.1, ES (−) 623.3.

EXAMPLE 24

S-3-[2-(7-chloro-1-oxo-1H-isoquinolin-2-yl)-butyry-lamino]-4-oxo-5-(2,3,5,6-tetrafluoro-phenoxy)-pentanoic acid cyclopentyl ester

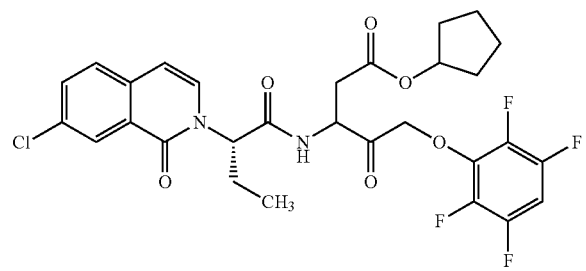

This was prepared using procedures similar to that described in Method N. The product was isolated as a white solid (40%); IR (solid) 1639, 1509, 1485, 841; $^1$H NMR (400 MHz, CDCl$_3$) δ 0.96-1.01 (3H, m), 1.56-1.89 (9H, m), 1.97-2.02 (1H, m), 2.27-2.32 (1H, m), 2.76 (1H, 2dd), 3.02 (1H, 2dd), 4.74-5.16 (2H, 2dd), 4.88-4.92 (1H, m), 5.44 (1H, dd), 6.57 (1H, dd), 6.70-6.82 (1H, m), 7.26 (1H, d), 7.41-7.52 (2H, m), 7.73 (1H, dd), 8.37 (1H, dd); $^{19}$F (376 MHz, CDCl$_3$) δ −139.75, −139.77, −139.80, −139.83, −139.86, −157.01, −157.03, −157.07, −157.09, 157.13, −157.15, −157.19, −157.21; ES(+) 611.1, ES(−) 609.2.

EXAMPLE 25

S-3-[2-(7-chloro-1-oxo-1H-isoquinolin-2-yl)-butyry-lamino]-4-oxo-5-(2,3,5,6-tetrafluoro-phenoxy)-pentanoic acid tetrahydro-4H-pyran-4-ol ester

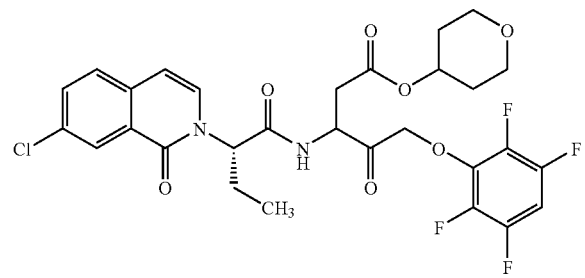

This was prepared using procedures similar to that described in Method N. The product was isolated as a white solid (41%); IR (solid) 1644, 1509, 1485, 827; $^1$H NMR (400 MHz, CDCl$_3$) δ 0.96-1.01 (3H, m), 1.43-1.91 (4H, m), 1.95-2.03 (1H, m), 2.27-2.35 (1H, m), 2.84 (1H, 2dd), 3.03 (1H, 2dd), 3.41-3.54 (2H, m), 3.78-3.94 (2H, m), 4.77-5.11 (4H, 3m), 5.44 (1H, dd), 6.59 (1H, dd), 6.72-6.85 (1H, m), 7.25 (1H, d), 7.32-7.51 (2H, m), 7.63 (1H, dd), 8.35 (1H, dd); $^{19}$F (376 MHz, CDCl$_3$) δ −139.68, −139.69, −139.70, −139.72, −139.73, −139.75, −139.76, −157.06, −157.08, −157.12, −157.14, −157.17, −157.19, −157.22, −157.25; ES (+) 627.2, ES(−) 625.3.

EXAMPLE 26

S-3-[2-(7-chloro-1-oxo-1H-isoquinolin-2-yl)-butyry-lamino]-4-oxo-5-(2,3,5,6-tetrafluoro-phenoxy)-pentanoic acid 1sobutyl ester

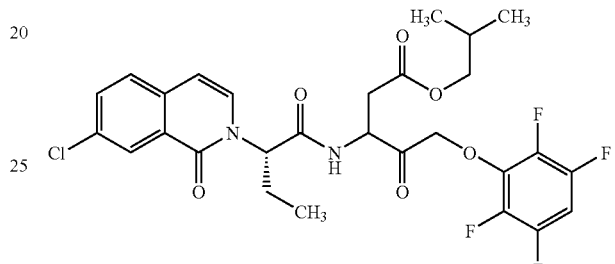

This was prepared using procedures similar to that described in Method N. The product was isolated as a white solid (72%); IR (solid) 1644, 1509, 1489, 832; $^1$H NMR (400 MHz, CDCl$_3$) δ 0.84-0.91 (6H, 2dd), 0.92-1.00 (3H, m), 1.79-2.02 (2H, m), 2.25-2.33 (1H, m), 2.80-2.91 (1H, m), 3.03 (1H, 2dd), 3.73 & 3.87 (2H, 2d), 4.74-5.10 (3H, m), 5.43-5.47 (1H, m), 6.57-6.59 (1H, m), 7.69-7.81 (1H, m), 7.24 (1H, d), 7.44-7.51 (2H, m), 7.62 (1H, dd), 8.39 (1H, dd); $^{19}$F (376 MHz, CDCl$_3$) δ −139.75, −139.78, −139.80, −139.81, −139.83, −139.83, −139.85, −157.04, −157.06, −157.10, −157.12, −157.16, −157.18, −157.22, −157.24; ES(+) 599.2, ES(−) 597.3.

EXAMPLE 27

S-3-[2-(7-chloro-1-oxo-1H-isoquinolin-2-yl)-butyry-lamino]-4-oxo-5-(2,3,5,6-tetrafluoro-phenoxy)-pentanoic acid 3-pentanol ester

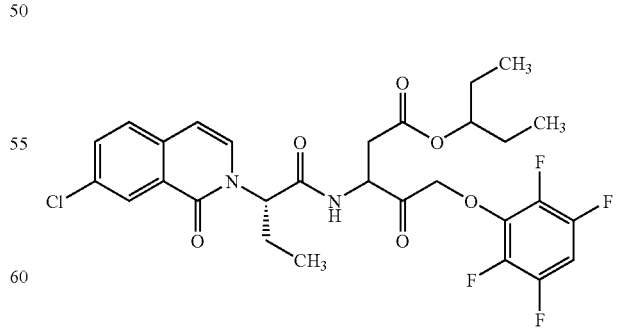

This was prepared using procedures similar to that described in Method N. The product was isolated as a white solid (23%); IR (solid) 1644, 1601, 1518, 1485, 832; $^1$H NMR (400 MHz, CDCl$_3$) δ 0.77-0.89 (6H, m), 0.96-0.99 (3H, m), 1.41-1.55 (4H, m), 1.97-2.03 (1H, m), 2.26-2.34 (1H, m), 2.81 (1H, 2dd), 3.04 (1H, 2dd), 4.75-5.12 (4H, m), 5.43-5.46 (1H, m), 6.56-6.59 (1H, m), 7.71-7.84 (1H, m), 7.24 (1H, d), 7.32-7.51 (2H, m), 7.61-7.63 (1H, m), 8.37 (1H, dd); $^{19}$F (376 MHz, CDCl$_3$) δ −139.80, −139.80, −139.82, −139.84, −139.86, −139.88, −139.89, −139.92, −157.02, −157.05, −157.08, −157.10, −157.13, −157.15, −157.18, −157.21; ES(+) 613.1, ES(−) 611.3.

EXAMPLE 28

S-3-[2-(7-chloro-1-oxo-1H-isoquinolin-2-yl)-butyrylamino]-4-oxo-5-(2,3,5,6-tetrafluoro-phenoxy)-pentanoic acid cycloheptanol ester

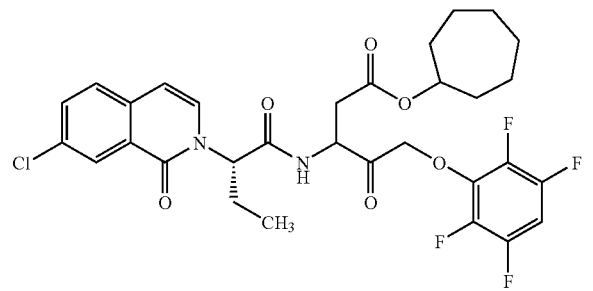

This was prepared using procedures similar to that described in Method N. The product was isolated as a white solid (11%); IR (solid)2936, 1645, 1509, 1489, 1093, 939, 827; $^1$H NMR (400 MHz, CDCl$_3$) δ 0.96-1.00 (3H, m), 1.42-1.60 (11H, m), 1.68-1.81 (1H, m), 1.82-1.91 (1H, m), 1.95-2.04 (1H, m), 2.26-2.33 (1H, m), 2.77 (1H, m), 3.03 (1H, m), 4.74-4.93 (2H, 2m), 5.09 (1H, dd), 5.45 (1H, dd), 6.57-6.59 (1H, m), 6.71-6.83 (1H, m), 7.24-7.26 (1H, m), 7.31-7.45 (1H, m), 7.48-7.50 (1H, m), 7.60-7.64 (1H, m), 8.38 (1H, dd); $^{19}$F (376 MHz, CDCl$_3$) δ−139.33, −139.36, −139.39, −139.42, −139.76, −139.78, −139.80, −139.81, −139.83, −139.86, −156.64, −156.66, −156.69, −156.71, −156.97, −157.00, −157.03, −157.05, −157.06, −157.10, −157.12, −157.15, −157.18; ES(+) 639.2, ES(−) 637.3.

EXAMPLE 29

S-3-[2-(7-chloro-1-oxo-1H-isoquinolin-2-yl)-butyrylamino]-4-oxo-5-(2,3,5,6-tetrafluoro-phenoxy)-pentanoic acid 2-hyroxy-3-methylbutanol ester

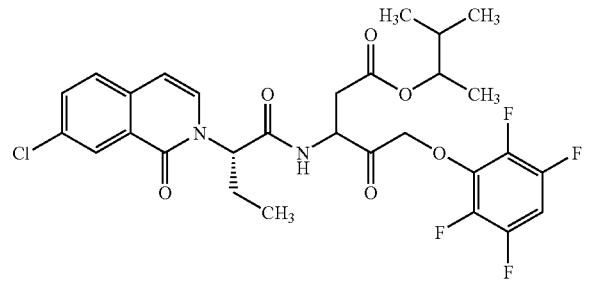

This was prepared using procedures similar to that described in Method N. The product was isolated as a white solid (24%); IR (solid) 1731, 1649, 1591, 1514, 1485, 1098, 929, 827; $^1$H NMR (400 MHz, CDCl$_3$) δ 0.80 (3H, d), 0.88 (3H, d), 0.96-1.00 (3H, m), 1.07-1.17 (3H, m), 1.63-1.71 (1H, m), 1.97-2.03 (1H, m), 2.25-2.32 (1H, m), 2.75-2.87 (1H, m), 2.93-3.12 (1H, m), 4.63-4.95 (3H, m), 5.08 (1H, dd), 5.42-5.46 (1H, m), 6.56-6.59 (1H, m), 6.68-6.82 (1H, m), 7.30 (1H, 2d), 7.41-7.55 (1H, m), 7.63 (1H, d), 8.36 (1H, m); $^{19}$F (376 MHz, CDCl$_3$) δ −139.39, −139.41, −139.43, −139.45, −139.77, −139.79, −139.82, −139.85, −139.87, −156.67, −156.69, −156.71, −156.74, −157.03, −157.05, −157.09, 157.11, −157.14, −157.16, −157.20, −157.22; ES(+) 613.3, ES(−) 611.3.

EXAMPLE 30

S-3-[2-(7-chloro-1-oxo-1H-isoquinolin-2-yl)-butyrylamino]-4-oxo-5-(2,3,5,6-tetrafluoro-phenoxy)-pentanoic acid 2-phenyl-2-methylpropanol ester

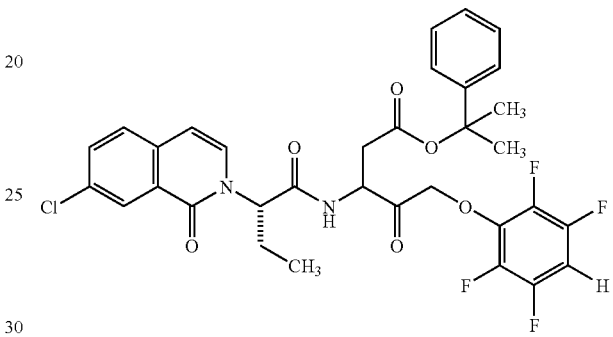

Method U

To a solution of S-3-[2-(7-chloro-1-oxo-1H-isoquinolin-2-yl)-butyrylamino]-4-oxo-5-(2,3,5,6-tetrafluoro-phenoxy)-pentanoic acid (100 mg) in dichloromethane (1 mL) was added a solution of 2-phenylpropan-2-yl 2,2,2-trichloroacetimidate (prepared as described in Tetrahedron Letters 1993, 34, 323-326) (103 mg)in cyclohexane (2 ml). The resulting mixture was stirred at room temperature for 3 days, then concentrated in vacuo. The residue was purified by column chromatography (25% ethyl acetate/hexane). The compound was further purified by slurrying in cyclohexane/dichloromethane. This afforded the title compound as a white solid (65 mg, 53%); IR (solid) 1731, 1690. 1654, 1516, 1485; $^1$H NMR (400 MHz, CDCl$_3$) δ 1.01 (3H, t), 1.68 (6H, ds), 1.99 (1H, m), 2.25 (1H, m), 2.82 (1H, dd), 3.05 (1H, dd), 4.85 (1H, m), 5.00 (2H, m), 5.42 (1H, m), 6.56 (1H, d), 6.80 (1H, m), 7.19-7.35 (7H, m), 7.49 (1H, m), 7.61 (1H, m), 8.38 (1H, m); ES(+) 661.33, ES(−) 659.33.

EXAMPLE 31

S-3-[2-(7-chloro-1-oxo-1H-isoquinolin-2-yl)-butyrylamino]-4-oxo-5-(2,3,5,6-tetrafluoro-phenoxy)-pentanoic acid 2-methyl-3-butyn-2-ol ester

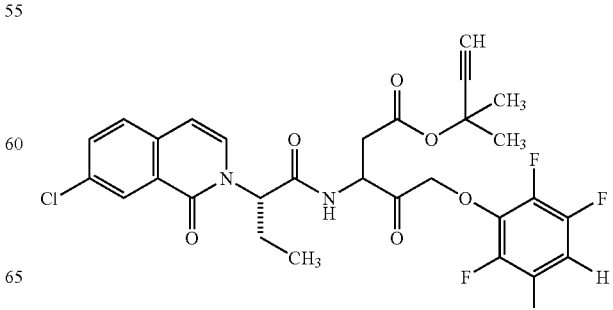

This was prepared using procedures similar to that described in Method U (Catalytic boron trifluoride diethyl ether complex was added to the reaction mixture, 1,1-dimethylpropionyl 2,2,2-trichloroacetimidate was prepared as described in J. Org. Chem. 2001, 66, 7568). The product was isolated as a white solid (30%); $^1$H NMR (400 MHz, CDCl$_3$) δ 1.00 (3H, m), 1.60 (6H, s), 2.01 (1H, m), 2.30 (1H, m), 2.50 (0.77H, s), 2.59 (0.23H, s), 2.77-3.14 (2H, m), 4.75-5.20 (3H, m), 5.51 (1H, m), 6.60 (1H, d), 6.80 (1H, m), 7.20-7.40 (2H, m), 7.50 (1H, d), 7.65 (1H, d), 8.40 (1H, s); $^{19}$F (376 MHz, CDCl$_3$) δ −139.76, −139.79, −139.81, −139.82, −139.83, −139.86, −139.89, −157.03, −157.05, −157.09, −157.11, −157.13, −157.16, −157.19, −157.22; ES(+) 609.29, ES(−) 607.26.

EXAMPLE 32

(S)-3-[2-(7-Chloro-1-oxo-1H-isoquinolin-2-yl)-butyrylamino]-4-oxo-5-(2,3,5,6-tetrafluoro-phenoxy)-pentanoic acid methoxy-methyl-amide

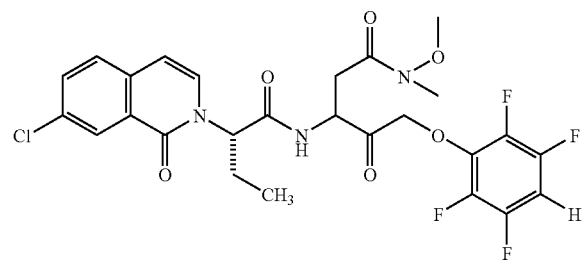

This was prepared using procedures similar to that described in Method N. The product was isolated as a white solid (67%); IR (solid)2970, 1645, 1514, 1495, 1093, 997, 943, 836; $^1$H NMR (400 MHz, CDCl$_3$) δ 0.95-103 (3H, m), 1.94-2.03 (1H, m), 2.21-2.32 (1H, m), 2.85 (1H, dd), 3.05 & 3.16 (3H, 2×s), 3.32 (1H, m), 3.61 & 3.72 (3H, 2s), 4.73-4.98 (2H, 2m), 5.18 (1H, dd), 5.40-5.49 (1H, m), 6.56-6.59 (1H, m), 6.69-6.81 (1H, m), 7.36-7.62 (4H, m), 8.37 (1H, dd); $^{19}$F (376 MHz, CDCl$_3$) δ −139.99, −140.01, −140.03, −140.04, −140.06, −140.09, −156.94, −156.96, −156.99, −157.02, −157.08, −157.01, −157.13, −157.16; ES(+) 586.2, ES(−) 584.2.

The documents cited herein are hereby incorporated by reference.

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments that have been represented by way of example above.

We claim:
1. A compound selected from the following:

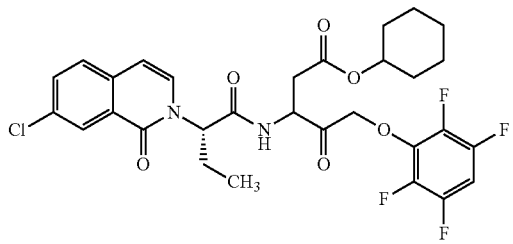

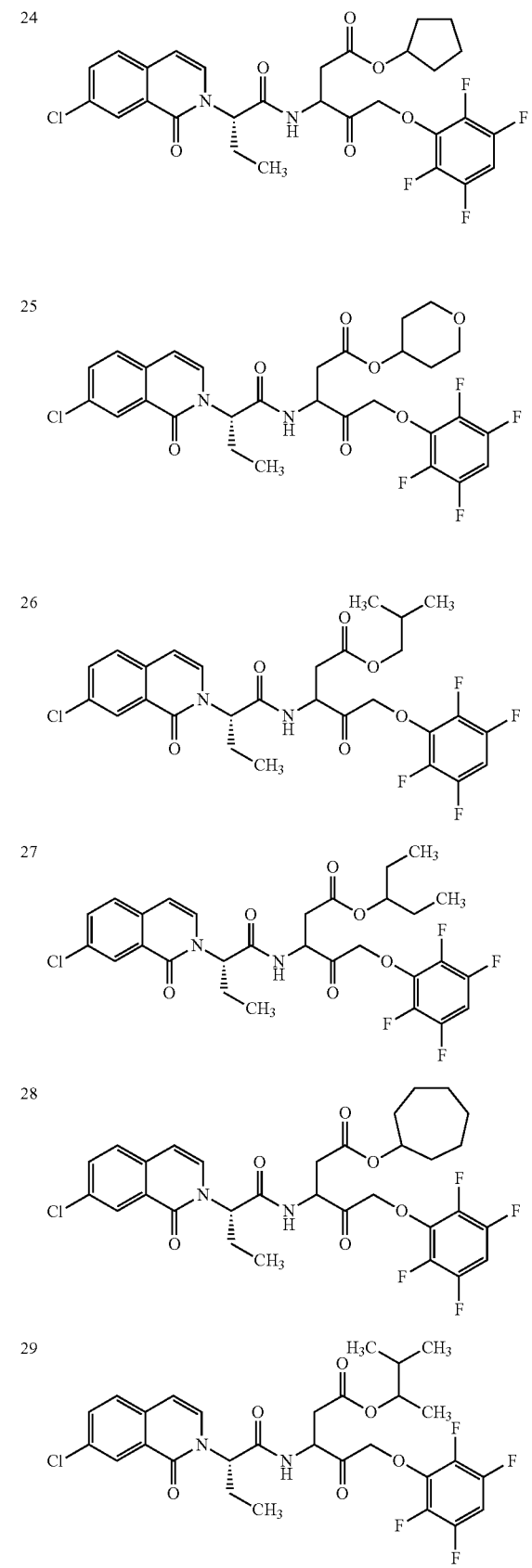

| 71 -continued | 72 -continued |
|---|---|
| 30 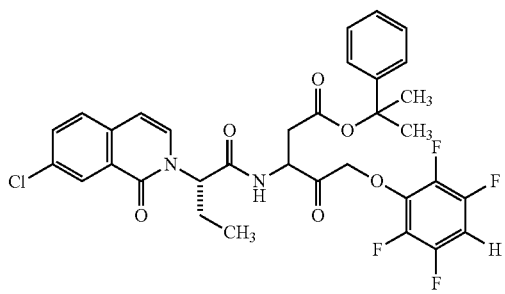 | 36 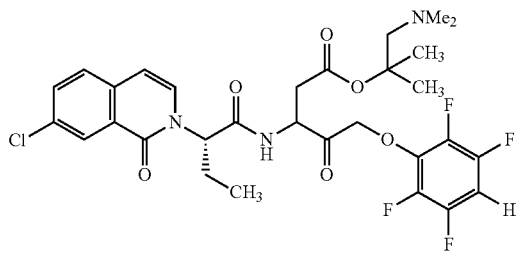 |
| 31 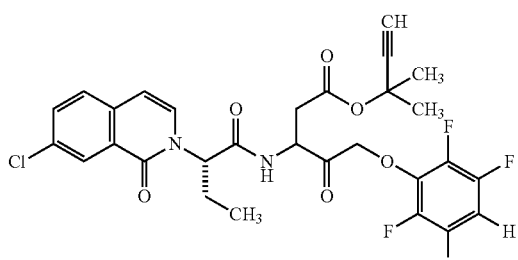 | 37 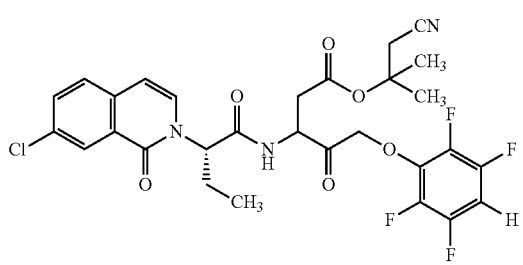 |
| 32 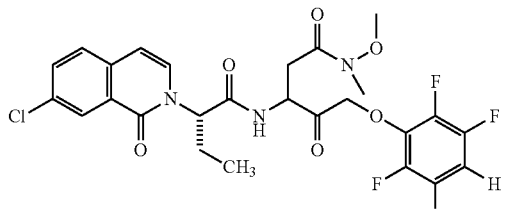 | 38 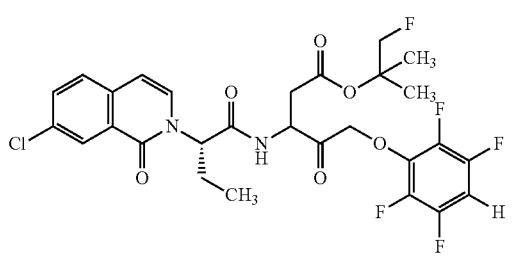 |
| 33 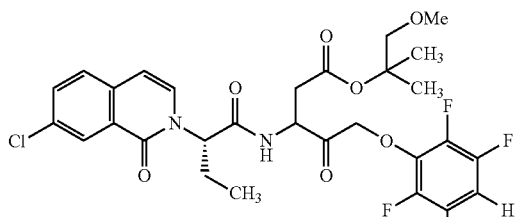 | 39 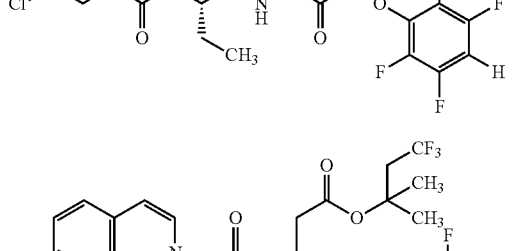 |
| 34 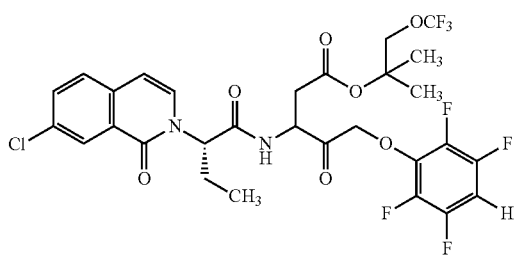 | 40 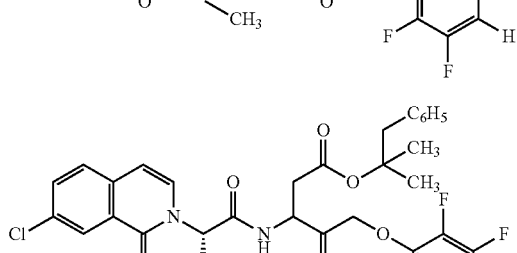 |
| 35 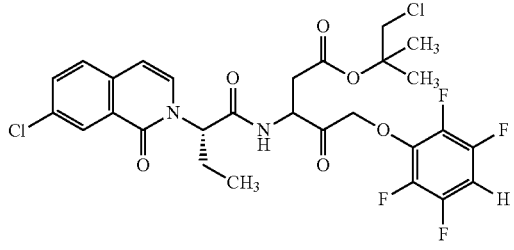 | 41 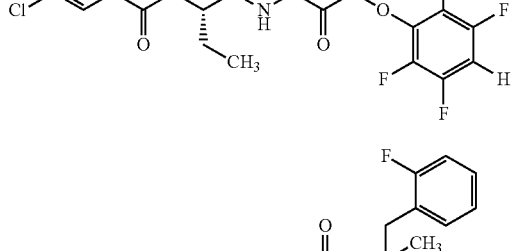 |

| 73 -continued | 74 -continued |
|---|---|
| 42 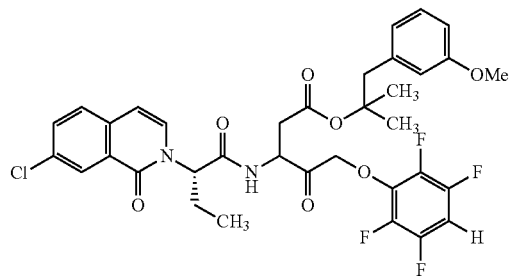 | 47 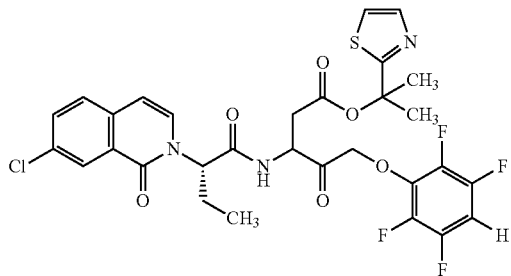 |
| 43 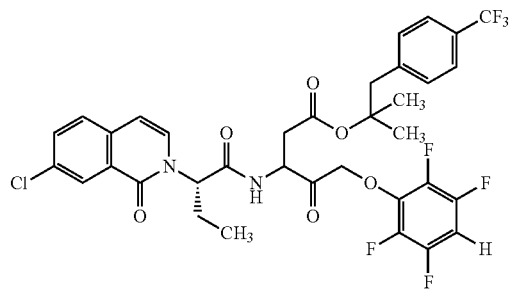 | 48 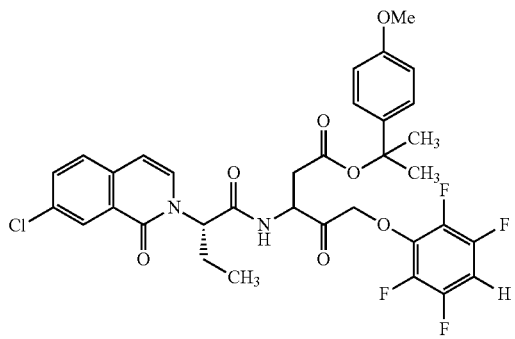 |
| 44 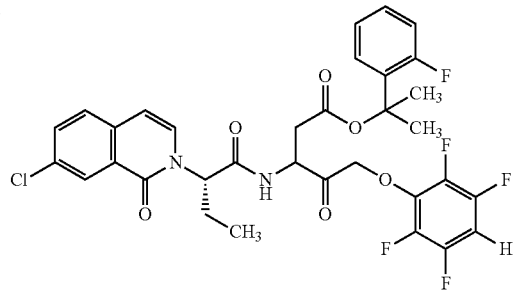 | 49 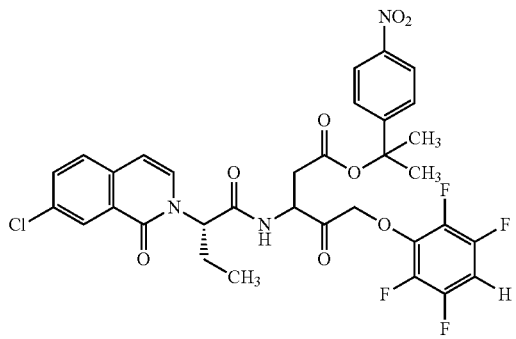 |
| 45 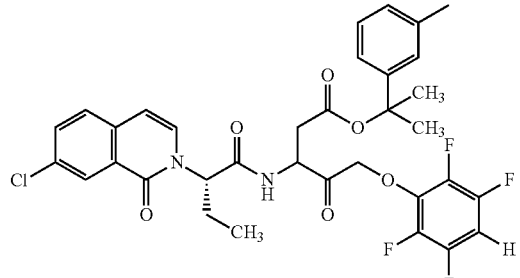 | 50 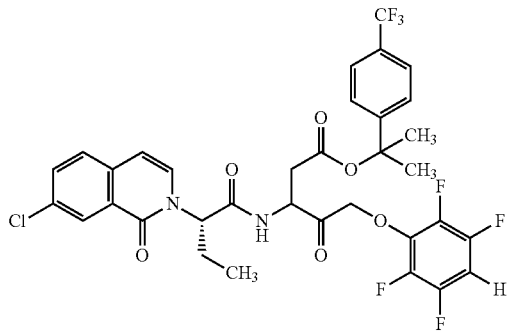 |
| 46 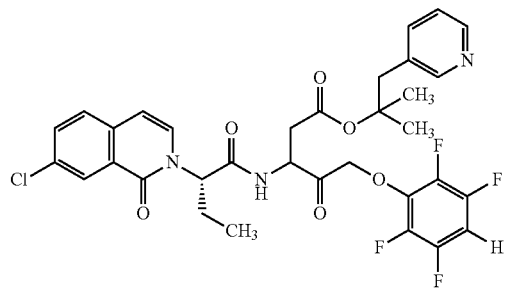 | 51 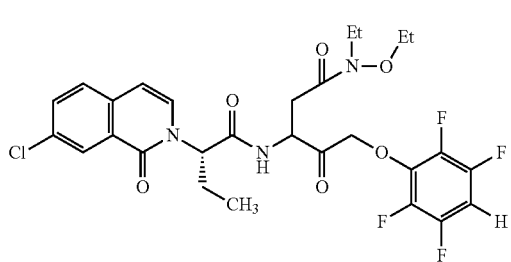 |

| 75 -continued | 76 -continued |
|---|---|
| 52 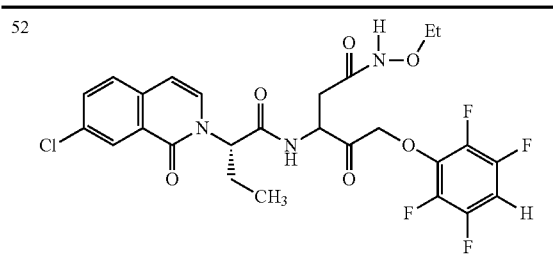 | 56 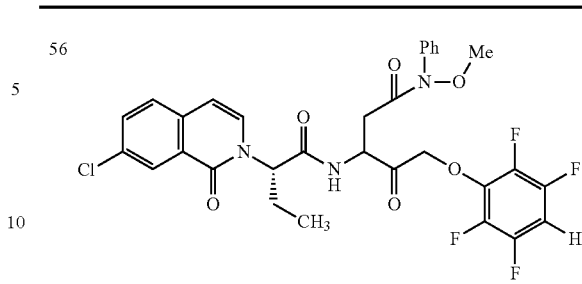 |
| 53 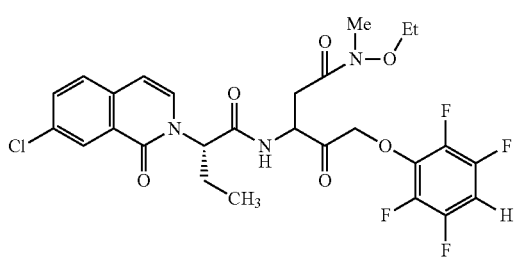 | 57 |
| 54 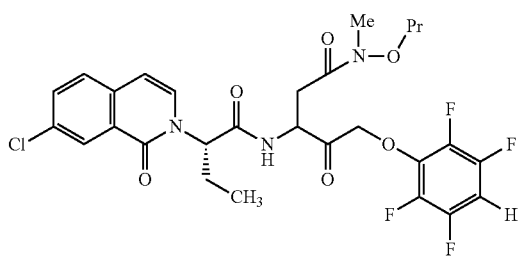 | 58 |
| 55 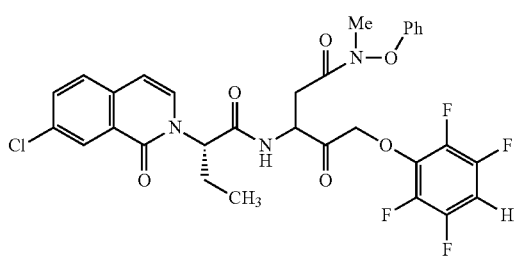 | 59 |

60 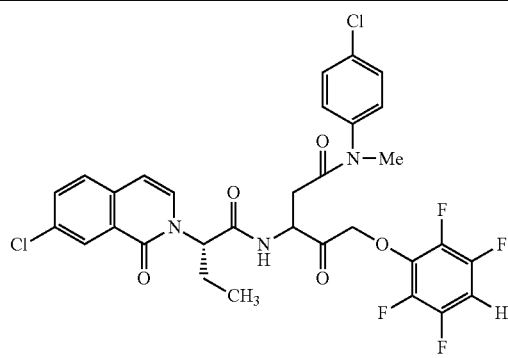
61 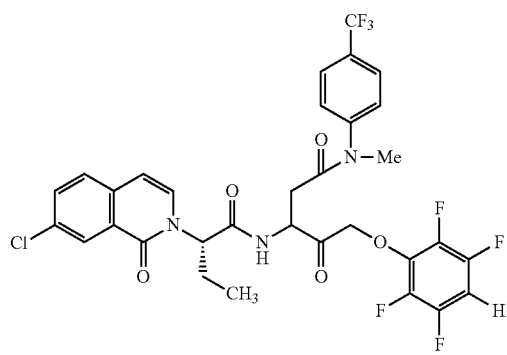
62 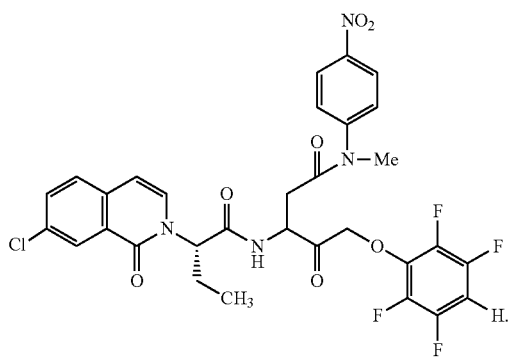
2. A pharmaceutical composition comprising:
a) a compound according to claim 1; and
b) a pharmaceutically acceptable carrier, adjuvant or vehicle.
* * * * *